(12) United States Patent
Schaper et al.

(10) Patent No.: US 7,332,509 B2
(45) Date of Patent: Feb. 19, 2008

(54) HETEROCYCLIC AMIDES, A PROCESS FOR THEIR PREPARATION, COMPOSITIONS COMPRISING THEM AND THEIR USE

(75) Inventors: Wolfgang Schaper, Diedorf (DE); Marion Beckmann, Wiesbaden (DE); Uwe Döller, Rodgau (DE); Gerhard Krautstrunk, Bad Vilbel (DE); Daniela Jans, Bad Homburg v.d.H. (DE); Waltraud Hempel, Liederbach (DE); Jutta Maria Waibel, Frankfurt (DE)

(73) Assignee: Merial Limited, Duluth, GA (US)

( * ) Notice: Subject to any disclaimer, the term of this patent is extended or adjusted under 35 U.S.C. 154(b) by 187 days.

(21) Appl. No.: 10/255,288

(22) Filed: Sep. 26, 2002

(65) Prior Publication Data

US 2004/0006047 A1    Jan. 8, 2004

(30) Foreign Application Priority Data

Sep. 29, 2001   (DE) ................................ 101 48 290

(51) Int. Cl.
| | |
|---|---|
| C07D 401/06 | (2006.01) |
| C07D 405/06 | (2006.01) |
| C07D 415/06 | (2006.01) |
| A01N 43/40 | (2006.01) |
| C07D 239/24 | (2006.01) |
| A61K 31/506 | (2006.01) |

(52) U.S. Cl. .................................. 514/336; 546/268.1
(58) Field of Classification Search ............. 546/268.1; 514/336
See application file for complete search history.

(56) References Cited

U.S. PATENT DOCUMENTS 6,534,445 B1 * 3/2003 Edmunds et al. ........... 504/130

FOREIGN PATENT DOCUMENTS

| | | |
|---|---|---|
| DE | 100 14 006 A1 * | 9/2001 |
| EP | 0 580 374 | 1/1994 |
| EP | 0 799 825 A1 | 10/1997 |
| JP | 10195072 | 7/1998 |
| WO | WO 96/11690 | 4/1996 |
| WO | WO-00/39094 A1 * | 7/2000 |
| WO | WO 01/70692 A2 | 9/2001 |

* cited by examiner

Primary Examiner—Venkataraman Balasubramanian
(74) Attorney, Agent, or Firm—Judy Jarecki-Black; Frommer, Lawrence & Haug

(57) ABSTRACT

What is described are amides of the formula (I) and salts thereof,

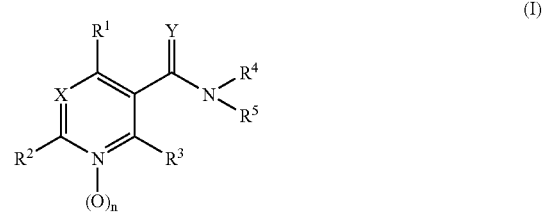

(I)

where the symbols and indices are as defined below:
X is CH or N; Y is O or S;
n is 0 or 1; $R^1$ is $(C_1-C_4)$-haloalkyl;
$R^2$, $R^3$ independently of one another are hydrogen, $(C_1-C_4)$-alkyl, $(C_1-C_4)$-haloalkyl or halogen,
$R^4$ is hydrogen, $(C_1-C_{10})$-alkyl, $(C_3-C_{10})$-cycloalkyl, $(C_3-C_{10})$-alkenyl or $(C_3-C_{10})$-alkynyl, where in the alkyl, cycloalkyl, alkenyl or alkynyl groups mentioned up to three hydrogen atoms may be replaced by halogen, in the case of fluorine also up to the maximum number;
$R^5$ is an aliphatic heterocycle which contains at least one oxygen, sulfur, nitrogen and/or silicon ring atom, which is unsubstituted or substituted by one to six monovalent groups and which may be part of a spirocyclic, fused or bicyclic ring system.

These compounds can be used for controlling pests.

18 Claims, No Drawings

HETEROCYCLIC AMIDES, A PROCESS FOR THEIR PREPARATION, COMPOSITIONS COMPRISING THEM AND THEIR USE

The invention relates to heterocyclic amides, to processes for their preparation, to compositions comprising them and to their use for controlling animal pests, in particular arthropods, such as insects and acarids, and helminths.

Owing to the enormous damage caused by insects, for example by feeding on useful plants, stored food, wood and textiles, or else by transferring diseases to man, domestic animals and useful plants, the use of insecticides or repellents is still indispensable. Insecticides are an important component of integrated pest control, and their contribution is decisive with respect to harvest yield and harvest continuity all over the world.

EP-A 0 580 374 discloses trifluoromethylpyridinamides for use as pesticides.

However, since the ecological and economical demands made on modern insecticides are increasing constantly, for example with respect to toxicity, selectivity, application rate, formation of residues and favorable manufacture, and there can furthermore be problems, for example, with resistance, there is a constant need to develop novel insecticides which, at least in some areas, have advantages over those of the prior art.

It has been found that compounds of the formula (I), if appropriate also as salts, have a good activity spectrum against animal pests and at the same time good plant tolerance and favorable toxicological properties with respect to mammals and aquatic animals.

Accordingly, the present invention provides amides of the formula (I) and salts thereof

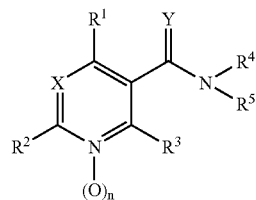

(I)

where the symbols and indices are as defined below:
X is CH or N;
Y is O or S;
n is 0 or 1;
$R^1$ is $(C_1-C_4)$-haloalkyl;
$R^2$, $R^3$ independently of one another are hydrogen, $(C_1-C_4)$-alkyl, $(C_1-C_4)$-haloalkyl or halogen;
$R^4$ is hydrogen, $(C_1-C_{10})$-alkyl, $(C_3-C_{10})$-cycloalkyl, $(C_3-C_{10})$-alkenyl or $(C_3-C_{10})$-alkynyl, where the alkyl, cycloalkyl, alkenyl or alkynyl groups are unsubstituted or substituted by up to three halogen atoms, preferably fluorine or chlorine, in the case of fluorine also up to the maximum number;
$R^5$ is an aliphatic heterocycle, which is preferably four- to eight-membered and contains at least one oxygen, sulfur, nitrogen and/or silicon ring atom and which may be part of a spirocyclic, fused or bicyclic ring system.

$R^5$ is preferably a four- to eight-membered aliphatic heterocycle which contains one oxygen ring atom, one sulfur ring atom, one nitrogen ring atom, one silicon ring atom, two oxygen ring atoms or two sulfur ring atoms, where the sulfur ring atoms are present in the form —S(O)$_p$— and p is 0, 1 or 2.

With very particular preference, $R^5$ is a four- to eight-membered heteroaliphatic radical of the formula (II)

(II)

where A and/or B is/are a unit which contains at least one oxygen, sulfur, nitrogen or silicon ring atom, preferably —O—, —S(O)$_{0,1,2}$—, —NR$^8$— or —SiR$^9$R$^{10}$—, and where the ring may additionally contain one or two carbonyl groups which, together with the hetero units, may form a lactone, lactam or imide unit; and where, if A is oxygen and B is nitrogen, these units may be directly adjacent and where in all other cases in which A and B are heteroatom units these must be separated by at least one saturated carbon unit;
m is 0 or 1 to 6, preferably 0, 1 or 2;
$R^6$ are, depending on m, identical or different and are each a monovalent substituent of the heterocycloaliphatic ring, such as $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl or $(C_8-C_{10})$-cycloalkynyl which is unsubstituted or substituted by one or more identical or different radicals, or is/are a radical $R^7$, where
$R^7$ is halogen, cyano, nitro, hydroxyl, thio, amino, $(C_1-C_{10})$-alkanoyl, $(C_3-C_{10})$-alkenoyl, $(C_3-C_{10})$-alkynoyl, $(C_3-C_{10})$-cycloalkanoyl, $(C_1-C_{10})$-alkoxy, $(C_3-C_{10})$-alkenyloxy, $(C_3-C_{10})$-alkynyloxy, $(C_3-C_{10})$-cycloalkoxy, $(C_4-C_{10})$-cycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_3-C_4)$-alkenyloxy, $(C_4-C_8)$-cycloalkenyl-$(C_3-C_4)$-alkenyloxy, $(C_1-C_4)$-alkyl-$(C_3-C_8)$-cycloalkoxy, $(C_2-C_4)$-alkenyl-$(C_3-C_8)$-cycloalkoxy, $(C_2-C_4)$-alkynyl-$(C_3-C_8)$-cycloalkoxy, $(C_1-C_4)$-alkyl-$(C_4-C_8)$-cycloalkenyloxy, $(C_2-C_4)$-alkenyl-$(C_4-C_8)$-cycloalkenyloxy, $(C_1-C_4)$-alkoxy-$(C_1-C_4)$-alkoxy, $(C_1-C_4)$-alkoxy-$(C_3-C_4)$-alkenyloxy, carbamoyl, $(C_1-C_8)$-mono- or -dialkylcarbamoyl, $(C_3-C_8)$-mono- or -dicycloalkylcarbamoyl, $(C_1-C_8)$-alkoxycarbonyl, $(C_3-C_8)$-cycloalkoxycarbonyl, $(C_1-C_8)$-alkanoyloxy, $(C_3-C_8)$-cycloalkanoyloxy, $(C_1-C_8)$-alkanoylamino, $(C_3-C_8)$-alkenoylamino, $(C_3-C_8)$-cycloalkanoyl-amino, $(C_3-C_8)$-cycloalkyl-$(C_1-C_4)$-alkanoylamino, the N-$(C_1-C_4)$-alkylamino analogs of the four last-mentioned radicals, $(C_1-C_{10})$-alkylthio, $(C_3-C_{10})$-alkenylthio, $(C_3-C_{10})$-alkynylthio, $(C_3-C_8)$-cycloalkylthio, $(C_4-C_8)$-cycloalkenylthio, $(C_3-C_8)$-cycloalkyl-$(C_1-C_4)$-alkylthio, $(C_4-C_8)$-cycloalkenyl-$(C_1-C_4)$-alkylthio, $(C_3-C_8)$-cycloalkyl-$(C_3-C_4)$-alkenylthio, $(C_4-C_8)$-cycloalkenyl-$(C_3-C_4)$-alkenylthio, $(C_1-C_4)$-alkyl-$(C_3-C_8)$-cycloalkylthio, $(C_2-C_4)$-alkenyl-$(C_3-C_8)$-cycloalkylthio, $(C_2-C_4)$-alkynyl-$(C_3-C_8)$-cycloalkylthio, $(C_1-C_8)$-alkyl-$(C_4-C_8)$-cycloalkenylthio, $(C_2-C_6)$-alkenyl-$(C_4-C_8)$-cycloalkenylthio, $(C_1-C_{10})$-alkylsulfinyl, $(C_3-C_4)$-alkenylsulfinyl, $(C_3-C_4)$-alkynylsulfinyl, $(C_3-C_{10})$-cycloalkylsulfinyl, $(C_4-C_{10})$-cycloalkenylsulfinyl, $(C_3-C_8)$-cycloalkyl-$(C_1-C_4)$-alkylsulfinyl, $(C_4-C_8)$-cycloalkenyl-$(C_1-C_4)$-alkylsulfinyl, $(C_3-C_8)$-cycloalkyl-$(C_3-C_4)$-alkenylsulfinyl, $(C_4-C_8)$-cycloalkenyl-$(C_3-C_4)$- alkenylsulfinyl, $(C_1-C_4)$-alkyl-$(C_3-C_8)$-cycloalkylsulfinyl, $(C_2-C_4)$-alkenyl-$(C_3-C_8)$-cycloalkylsulfinyl, $(C_2-C_4)$-alkynyl-$(C_3-C_8)$-cycloalkylsulfinyl, $(C_1-C_4)$-alkyl-$(C_4-C_8)$-cycloalkenylsulfinyl, $(C_2-C_3)$-alkenyl-$(C_4-C_8)$-cycloalkenylsulfinyl, $(C_1-C_{10})$-alkylsulfonyl, $(C_3-C_{10})$-alkenylsulfonyl, $(C_3-C_{10})$-alkynylsulfonyl, $(C_3-C_{10})$-cycloalkylsulfonyl, $(C_4-C_{10})$-cycloalkenylsulfonyl, $(C_3-C_8)$-cycloalkyl-$(C_1-C_4)$-alkylsulfonyl, $(C_4-C_8)$-cycloalkenyl-$(C_1-C_4)$-alkylsulfonyl, $(C_3-C_8)$-cycloalkyl-$(C_3-C_4)$-alkenylsulfonyl, $(C_4-C_8)$-cycloalkenyl-$(C_3-C_4)$-alkenylsulfonyl, $(C_1-C_4)$-alkyl-$(C_3-C_8)$-cycloalkylsulfonyl, $(C_2-C_4)$-alkenyl-$(C_3-C_8)$-cycloalkylsulfonyl, $(C_3-C_6)$-alkynyl-$(C_3-C_8)$-cycloalkylsulfonyl, $(C_1-C_4)$-alkyl-$(C_4-C_8)$-cycloalkenylsulfonyl, $(C_3-C_4)$-alkenyl-$(C_4-C_8)$-cycloalkenylsulfonyl, $(C_1-C_{10})$-alkylamino, $(C_3-C_{10})$-alkenylamino, $(C_3-C_{10})$-alkynylamino, $(C_3-C_8)$-cycloalkylamino, $(C_4-C_8)$-cycloalkenylamino, $(C_3-C_8)$-cycloalkyl-$(C_1-C_4)$-alkylamino, $(C_4-C_8)$-cycloalkenyl-$(C_1-C_4)$-alkylamino, $(C_3-C_8)$-cycloalkyl-$(C_3-C_4)$-alkenylamino, $(C_4-C_8)$-cycloalkenyl-$(C_3-C_4)$-alkenylamino, $(C_1-C_4)$-alkyl-$(C_3-C_8)$-cycloalkylamino, $(C_2-C_4)$-alkenyl-$(C_3-C_8)$-cycloalkylamino, $(C_2-C_4)$-alkynyl-$(C_3-C_8)$-cycloalkylamino, $(C_1-C_4)$-alkyl-$(C_3-C_8)$-cycloalkenylamino, $(C_2-C_4)$-alkenyl-$(C_4-C_8)$-cycloalkenylamino, the N-$(C_1-C_4)$-alkylamino analogs of the fourteen last-mentioned radicals, $(C_1-C_{10})$-trialkylsilyl, aryl, aroyl, heterocyclylcarbonyl, aryloxy, arylthio, arylamino, N-$(C_1-C_4)$-alkyl-arylamino, the N-$(C_1-C_4)$-alkylamino analogs of the two last-mentioned radicals, aryl-$(C_1-C_4)$-alkoxy, aryl-$(C_3-C_4)$-alkenyloxy, aryl-$(C_1-C_4)$-alkylthio, aryl-$(C_3-C_4)$-alkenylthio, aryl-$(C_1-C_4)$-alkylamino, aryl-$(C_3-C_4)$-alkenylamino, the N-$(C_1-C_4)$-alkylamino analog of the last-mentioned radical, aryl-$(C_1-C_8)$-dialkylsilyl, diaryl-$(C_1-C_8)$-alkylsilyl, triarylsilyl, heterocyclyl, heterocyclyloxy, heterocyclylthio or heterocyclylamino, where the cyclic moiety of the aryl or heterocyclyl radicals mentioned is unsubstituted or substituted by one or more radicals selected from the group consisting of halogen, cyano, nitro, amino, hydroxyl, thio, $(C_1-C_4)$-alkyl, $(C_1-C_4)$-haloalkyl, $(C_3-C_8)$-cycloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylamino, $(C_1-C_4)$-dialkylamino, trimethylsilyl and $(C_1-C_4)$-alkanoyl;

where, if appropriate, two alkyl radicals $R^6$ attached to the same carbon atom may form, together with this carbon atom, a spirocyclic ring system, or where, if appropriate, two alkyl radicals $R^6$ attached to different carbon atoms may, together with the aliphatic heterocycle of the formula (II), form a fused or bicyclic ring system or furthermore the heteroaliphatic ring system of the formula (II) and an additional aryl or heteroaryl system together may form a fused ring system;

and where, if $R^6$ is $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl oder $(C_8-C_{10})$-cycloalkynyl, the radicals mentioned are either unsubstituted or mono- or polysubstituted, preferably by radicals $R^{11}$, where $R^{11}$ has the meanings given above for $R^7$;

$R^8$ is hydrogen, $(C_1-C_{10})$-alkyl, $(C_3-C_{10})$-alkenyl, $(C_3-C_{10})$-alkynyl, $(C_3-C_{10})$-cycloalkyl, $(C_4-C_{10})$-cycloalkenyl, aryl, heterocyclyl, $(C_1-C_{10})$-alkanoyl, $(C_3-C_{10})$-alkenoyl, $(C_3-C_{10})$-alkynoyl, $(C_4-C_8)$-cycloalkanoyl, aroyl, heterocyclylcarbonyl, carbamoyl, $(C_1-C_6)$-mono- or -dialkylcarbamoyl, $(C_3-C_{10})$-mono- or -dicycloalkylcarbamoyl, $(C_1-C_{10})$-alkoxycarbonyl, $(C_3-C_{10})$-cycloalkoxycarbonyl, $(C_1-C_{10})$-alkylsulfonyl, $(C_3-C_{10})$-alkenylsulfonyl, $(C_3-C_6)$-alkynylsulfonyl, $(C_3-C_{10})$-cycloalkylsulfonyl, $(C_4-C_{10})$-cycloalkenylsulfonyl, $(C_3-C_{10})$-cycloalkyl-$(C_1-C_{10})$-alkylsulfonyl, $(C_4-C_8)$-cycloalkenyl-$(C_1-C_4)$-alkylsulfonyl, $(C_3-C_8)$-cycloalkyl-$(C_3-C_4)$-alkenylsulfonyl, $(C_4-C_8)$-cycloalkenyl-$(C_3-C_4)$-alkenylsulfonyl, $(C_1-C_4)$-alkyl-$(C_3-C_8)$-cycloalkylsulfonyl, $(C_2-C_4)$-alkenyl-$(C_3-C_8)$-cycloalkylsulfonyl, $(C_2-C_4)$-alkynyl-$(C_3-C_8)$-cycloalkylsulfonyl, $(C_1-C_4)$-alkyl-$(C_4-C_8)$-cycloalkenylsulfonyl, $(C_2-C_4)$-alkenyl-$(C_4-C_8)$-cycloalkenylsulfonyl, hydroxyl, $(C_1-C_{10})$-alkoxy, $(C_3-C_{10})$-alkenyloxy, $(C_3-C_{10})$-alkynyloxy, $(C_3-C_{10})$-cycloalkoxy, $(C_4-C_{10})$-cycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_3-C_4)$-alkenyloxy, $(C_4-C_8)$-cycloalkenyl-$(C_3-C_4)$-alkenyloxy, $(C_1-C_4)$-alkyl-$(C_3-C_8)$-cycloalkoxy, $(C_2-C_4)$-alkenyl-$(C_3-C_8)$-cycloalkoxy, $(C_2-C_4)$-alkynyl-$(C_3-C_8)$-cycloalkoxy, $(C_1-C_4)$-alkyl-$(C_4-C_8)$-cycloalkenyloxy, $(C_2-C_4)$-alkenyl-$(C_4-C_8)$-cycloalkenyloxy, $(C_1-C_4)$-alkoxy-$(C_1-C_4)$-alkoxy, $(C_1-C_4)$-alkoxy-$(C_3-C_4)$-alkenyloxy, aryloxy, aryl-$(C_1-C_{10})$-alkoxy, aryl-$(C_3-C_{10})$-alkenyloxy or aryl-$(C_3-C_{10})$-alkynyloxy, and where the radicals mentioned above for $R^8$ are either unsubstituted or substituted by one or more radicals selected from the group consisting of cyano, nitro, amino, hydroxyl, thio, $(C_1-C_4)$-alkyl, $(C_3-C_{10})$-cycloalkyl, $(C_1-C_4)$-alkoxy, $(C_1-C_4)$-alkylthio, $(C_1-C_4)$-alkylamino and $(C_1-C_4)$-alkanoyl;

$R^9$ and $R^{10}$ are $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl, $(C_8-C_{10})$-cycloalkynyl, aryl, aryl-$(C_1-C_4)$-alkyl or heterocyclyl, preferably methyl, and where, if appropriate, in all groups mentioned for $R^5$, $R^6$, $R^7$, $R^8$, $R^9$, $R^{10}$ and $R^{11}$ one to three hydrogens attached to carbon may be replaced by halogen atoms, in the case of fluorine also up to the maximum number.

The symbols and indices in the formula (I) are preferably as defined below:

x is preferably —CH—.

Y is preferably —O—.

n is preferably 0.

$R^1$ is preferably $(C_1-C_4)$-alkyl which is mono- or polysubstituted by F and/or Cl, with particular preference $CF_3$, $CHF_2$ or $CF_2Cl$, with very particular preference $CF_3$.

$R^2$, $R^3$ are preferably hydrogen.

$R^4$ is preferably hydrogen or methyl, with particular preference hydrogen.

Preference is furthermore given to compounds of the formula (I) in which $R^6$ is $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl or $(C_8-C_{10})$-cycloalkynyl, where the radicals mentioned are unsubstituted or mono- or polysubstituted by radicals $R^{11}$, $R^{11}$ having one of the meanings given above; with particular preference, $R^6$ is hydrogen or $(C_1-C_4)$-alkyl.

Preference is furthermore given to compounds of the formula (I) in which $R^5$ is preferably a five- to seven-membered aliphatic heterocycle having one or two heteroatom units A and/or B, with very particular preference a five- to seven-membered aliphatic heterocycle having one or two heteroatom units and, if appropriate, additionally a carbonyl group in the ring, which carbonyl group together with a hetero unit forms a lactone or lactam unit.

Preference is furthermore given to compounds of the formula (I) in which $R^7$ is aryl, aroyl, heterocyclylcarbonyl, aryloxy, arylthio, arylamino, N—($C_1$-$C_4$)-alkyl-arylamino, the N-($C_1$-$C_4$)-alkylamino analogs of the two last-mentioned radicals, aryl-($C_1$-$C_4$)-alkoxy, aryl-($C_3$-$C_4$)-alkenyloxy, aryl-($C_1$-$C_4$)-alkylthio, aryl-($C_3$-$C_4$)-alkenylthio, aryl-($C_1$-$C_4$)-alkylamino, aryl-($C_3$-$C_4$)-alkenylamino, the N-($C_1$-$C_4$)-alkylamino analog of the last-mentioned radical, aryl-($C_1$-$C_8$)-dialkylsilyl, diaryl-($C_1$-$C_8$)-alkylsilyl, triarylsilyl, heterocyclyl, heterocyclyloxy, heterocyclylthio or heterocyclylamino, where the cyclic moiety of the aryl or heterocyclyl radicals mentioned is unsubstituted or substituted by one or more radicals selected from the group consisting of halogen, cyano, nitro, amino, hydroxyl, thio, ($C_1$-$C_4$)-alkyl, ($C_1$-$C_4$)-haloalkyl, ($C_3$-$C_8$)-cycloalkyl, ($C_1$-$C_4$)-alkoxy, ($C_1$-$C_4$)-alkylthio, ($C_1$-$C_4$)-alkylamino or ($C_1$-$C_4$)-alkanoyl Preference is furthermore given to compounds of the formula (I) in which $R^8$ is ($C_1$-$C_4$)-alkyl, ($C_1$-$C_4$)-alkanoyl, ($C_1$-$C_4$)-alkoxycarbonyl, ($C_1$-$C_4$)-alkylsulfonyl or ($C_1$-$C_4$)-dialkylcarbamoyl.

Preference is furthermore given to compounds of the formula (I) in which

A or B is oxygen, sulfur, SO, $SO_2$ or $NR^8$, in particular oxygen, sulfur, SO or $SO_2$.

Preference is furthermore given to compounds of the formula (I) in which $R^5$ is a five- or six-membered aliphatic heterocycle having a heteroatom unit A or B, which heteroatom unit is preferably oxygen, sulfur, S(O) or $S(O)_2$, and, if A or B is oxygen, if appropriate with an additional carbonyl group in the ring, which together with the oxygen atom, forms a lactone group.

The term "halogen" embraces fluorine, chlorine, bromine and iodine.

The term "($C_1$-$C_4$)-alkyl" is to be understood as meaning an unbranched or branched aliphatic and saturated hydrocarbon radical having 1, 2, 3 or 4 carbon atoms, such as, for example, the methyl, ethyl, propyl, isopropyl, 1-butyl, 2-butyl, isobutyl or tert-butyl radical.

Correspondingly, alkyl radicals having a larger range of carbon atoms are to be understood as meaning an unbranched or branched aliphatic and saturated hydrocarbon radical which contains a number of carbon atoms which corresponds to the stated range. Accordingly, the expression "($C_1$-$C_{10}$)-alkyl" embraces the abovementioned alkyl radicals, and also, for example, the pentyl, 2-methylbutyl, 1,1-dimethylpropyl, hexyl, heptyl, octyl, tert-octyl, nonyl or decyl radical.

"($C_1$-$C_4$)-Haloalkyl" is to be understood as meaning an alkyl group mentioned under the expression "($C_1$-$C_4$)-alkyl" in which one or more hydrogen atoms are replaced by the same number of identical or different halogen atoms, preferably by chlorine or fluorine, such as the trifluoromethyl, the 1- or 2-fluoroethyl, the 2,2,2-trifluoroethyl, the chloromethyl, the fluoromethyl, the difluoromethyl or the 1,1,2,2-tetrafluoroethyl group.

The terms "alkenyl" and "alkynyl" with a range of carbon atoms stated as prefix denote a straight-chain or branched hydrocarbon radical having a number of carbon atoms which corresponds to this stated range and which contains at least one multiple bond which can be located in any position of the respective saturated radical. "($C_3$-$C_{10}$)-Alkenyl" accordingly denotes, for example, the allyl, 2-methylpropenyl, 1- or 2-butenyl, pentenyl, 2-methylpentenyl, hexenyl, heptenyl, octenyl, nonenyl or decenyl group. "($C_2$-$C_{10}$)-Alkenyl" denotes, for example, the abovementioned groups, and additionally the vinyl group.

"($C_3$-$C_{10}$)-Alkynyl" denotes, for example, the propargyl, 2-methylpropynyl, 2-butynyl, pentynyl, 2-methylpentynyl, hexynyl, heptynyl, octynyl, nonynyl or decynyl group. "($C_2$-$C_{10}$)-Alkynyl" is to be understood as meaning the abovementioned radicals and also the ethynyl group.

"($C_3$-$C_{10}$)-Cycloalkyl" denotes monocyclic and saturated alkyl radicals, such as the cyclopropyl, cyclobutyl, cyclopentyl, cyclohexyl, cycloheptyl, cyclooctyl or cyclodecyl radical; bicyclic and saturated alkyl radicals, such as the norbornyl or bicyclo[2.2.2]octyl radical, or else condensed and saturated systems, such as, for example, the decahydronaphthyl radical.

"($C_3$-$C_{10}$)-Cycloalkenyl" denotes monocyclic alkyl radicals which contain at least one multiple bond, such as the cyclobutenyl, cyclopentenyl, cyclohexenyl, cycloheptenylcyclooctenyl or cyclodecenyl radical; bicyclic alkyl radicals which contain at least one multiple bond, such as the norbornenyl or bicyclo[2.2.2]octenyl radical, or else condensed systems which contain at least one multiple bond, such as, for example, the tetra-, hexa- or octahydronaphthyl radicals.

"($C_8$-$C_{10}$)-Cycloalkynyl" denotes the cyclooctynyl, cyclononynyl or cyclodecynyl radical.

"($C_1$-$C_{10}$)-Alkanoyl" denotes, for example, the formyl, acetyl, propionyl, butyryl, 2-methylbutyryl, pivaloyl, octanoyl or decanoyl group.

"($C_3$-$C_{10}$)-Alkenoyl" denotes, for example, the acryl, methacryl, crotonoyl, dimethylacryl or octenoyl group.

"($C_3$-$C_{10}$)-Alkynoyl" denotes, for example, the propynoyl, butynoyl, hexynoyl or octynoyl group.

"($C_3$-$C_{10}$)-Cycloalkanoyl" denotes, for example, cyclopropylcarbonyl, cyclobutylcarbonyl, cyclopentylcarbonyl, cyclohexylcarbonyl or cyclooctylcarbonyl.

"($C_1$-$C_4$)-Alkoxy" and "($C_1$-$C_{10}$)-alkoxy" are to be understood as meaning alkoxy groups whose hydrocarbon radicals have the meanings given under the terms "($C_1$-$C_4$)-alkyl" and "($C_1$-$C_{10}$)-alkyl", respectively.

"($C_3$-$C_{10}$)-Alkenyloxy", "($C_3$-$C_{10}$)-alkynyloxy", "($C_3$-$C_{10}$)-cycloalkoxy" and "($C_4$-$C_{10}$)-cycloalkenyloxy" are to be understood as meaning alkoxy groups whose hydrocarbon radicals have the meanings given under the expressions "($C_3$-$C_{10}$)-alkenyl", "($C_3$-$C_{10}$)-alkynyl", "($C_3$-$C_{10}$)-cycloalkyl" and "($C_4$-$C_{10}$)-cycloalkenyl", respectively.

"($C_3$-$C_8$)-Cycloalkyl-($C_1$-$C_4$)-alkoxy" denotes, for example, the cyclopropylmethoxy, cyclopropylethoxy, cyclobutylmethoxy, cyclopentylmethoxy, cyclohexylmethoxy or cyclohexylethoxy group.

"($C_4$-$C_8$)-Cycloalkenyl-($C_1$-$C_4$)-alkoxy" denotes, for example, the cyclobutenylmethoxy, cyclopentenylmethoxy, cyclohexenylmethoxy or cyclohexenylethoxy groups.

"($C_3$-$C_8$)-Cycloalkyl-($C_3$-$C_4$)-alkenyloxy" denotes, for example, the cyclopropylallyloxy, cyclobutylallyloxy or cyclopentylallyloxy group.

"($C_4$-$C_8$)-Cycloalkenyl-($C_3$-$C_4$)-alkenyloxy" denotes, for example, the cyclobutenylallyloxy or cyclopentenylallyloxy group.

"($C_1$-$C_4$)-Alkyl-($C_3$-$C_8$)-cycloalkoxy" denotes, for example, the methylcyclopentyloxy, ethylcyclopentyloxy, methylcyclohexyloxy or ethylcyclohexyloxy group.

"($C_2$-$C_4$)-Alkenyl-($C_3$-$C_8$)-cycloalkoxy" denotes, for example, the vinylcyclopentyloxy, allylcyclopentyloxy, vinylcyclohexyloxy or allylcyclohexyloxy group.

"$(C_2-C_4)$-Alkynyl-$(C_3-C_8)$-cycloalkoxy" denotes, for example, the ethynylcyclopentyloxy, propynylcyclopentyloxy, ethynylcyclohexyloxy or propynylcyclohexyloxy group.

"$(C_1-C_4)$-Alkyl-$(C_4-C_8)$-cycloalkenyloxy" denotes, for example, the methylcyclopentenyloxy, ethylcyclopentenyloxy, methylcyclohexenyloxy or ethylcyclohexenyloxy group.

"$(C_2-C_4)$-Alkenyl-$(C_3-C_8)$-cycloalkoxy" denotes, for example, the vinylcyclopentyloxy, allylcyclopentyloxy, vinylcyclohexyloxy or allylcyclohexyloxy group.

"$(C_2-C_4)$-Alkenyl-$(C_3-C_8)$-cycloalkenyloxy" denotes, for example, the vinylcyclopentenyloxy, allylcyclopentenyloxy, vinylcyclohexenyloxy or allylcyclohexenyloxy group.

"$(C_1-C_4)$-Alkoxy-$(C_1-C_4)$-alkoxy" denotes an alkoxy group as defined above which is substituted by a further alkoxy group, such as, for example, the ethoxymethoxy, 1-methoxyethoxy, 1-ethoxyethoxy or 1-methoxypropoxy group.

"$(C_1-C_4)$-Alkoxy-$(C_3-C_4)$-alkenyloxy" denotes, for example, the methoxyallyloxy or ethoxyallyloxy group.

"$(C_1-C_8)$-Mono- or -dialkylcarbamoyl" denotes, for example, the methyl-, ethyl-, propyl-, isopropyl-, butyl- or tert-butylcarbamoyl group or the dimethyl-, diethyl-, methylethyl- or diisopropylcarbamoyl group, but also cyclic derivatives, such as, for example, the pyrrolidino- or piperidinocarbamoyl group.

"$(C_3-C_8)$-Mono- or -dicycloalkylcarbamoyl" denotes, for example, the cyclopropyl-, cyclobutyl-, cyclopentyl- or cyclohexylcarbamoyl group, or the dicyclopropyl-, dicyclobutyl-, dicyclopentyl- or dicyclohexylcarbamoyl group.

"$(C_1-C_8)$-Alkoxycarbonyl" denotes, for example, the methoxycarbonyl, ethoxycarbonyl, propoxycarbonyl, isopropoxycarbonyl, butoxycarbonyl, isobutoxycarbonyl, sec-butoxycarbonyl or tert-butoxycarbonyl group.

"$(C_3-C_8)$-Cycloalkoxycarbonyl" denotes, for example, the cyclopropoxycarbonyl, cyclobutoxycarbonyl, cyclopentyloxycarbonyl or cyclohexyloxycarbonyl group.

"$(C_1-C_8)$-Alkanoyloxy" denotes, for example, the acetoxy, propionyloxy, butanoyloxy or pivaloyloxy group.

"$(C_3-C_8)$-Cycloalkanoyloxy" denotes, for example, the cyclopropylcarbonyloxy, cyclobutylcarbonyloxy, cyclopentylcarbonyloxy or cyclohexylcarbonyloxy group.

"$(C_1-C_8)$-Alkanoylamino" denotes, for example, the formylamino, acetylamino, propionylamino, isopropionylamino, butanoylamino or pivaloylamino group.

"$(C_3-C_8)$-Alkenoylamino" denotes, for example, the acrylamino, methacrylamino, dimethylacrylamino or crotonylamino group.

"$(C_3-C_8)$-Cycloalkanoylamino" denotes, for example, the cyclopropanoylamino, cyclobutanoylamino, cyclopentanoylamino or cyclohexanoylamino group.

"$(C_3-C_8)$-Cycloalkyl-$(C_1-C_4)$-alkanoylamino" denotes, for example, the cyclopropylacetylamino or cyclopentylacetylamino group.

"$(C_1-C_{10})$-Alkylthio" denotes an alkylthio group whose hydrocarbon radical has the meaning given under the expression "$(C_1-C_{10})$-alkyl".

"$(C_3-C_{10})$-Alkenylthio" denotes an alkylenylthio group whose hydrocarbon radical has the meaning given under the expression "$(C_3-C_{10})$-alkenyl".

"$(C_3-C_{10})$-Alkynylthio" denotes an alkylnylthio group whose hydrocarbon radical has the meaning given under the expression "$(C_3-C_{10})$-alkynyl".

"$(C_3-C_{10})$-Cycloalkylthio" denotes a cycloalkylthio group whose hydrocarbon radical has the meaning given under the expression "$(C_3-C_{10})$-cycloalkyl".

"$(C_4-C_{10})$-Cycloalkenylthio" denotes a cycloalkenylthio group whose hydrocarbon radical has the meaning given under the expression "$(C_4-C_{10})$-cycloalkenyl".

"$(C_3-C_8)$-Cycloalkyl-$(C_1-C_4)$-alkylthio" denotes, for example, the cyclopropylmethylthio, cyclopropylethylthio, cyclopentyl methylthio or cyclohexylmethylthio group.

"$(C_4-C_8)$-Cycloalkenyl-$(C_1-C_4)$-alkylthio" denotes, for example, the cyclopentenylmethylthio or cyclohexenylmethylthio group.

"$(C_3-C_8)$-Cycloalkyl-$(C_3-C_4)$-alkenylthio" denotes, for example, the cyclopropylallylthio, cyclopentylallylthio or cyclohexylallylthio group.

"$(C_4-C_8)$-Cycloalkenyl-$(C_3-C_4)$-alkenylthio" denotes, for example, the cyclopentenylallylthio or cyclohexenylallylthio group.

"$(C_1-C_4)$-Alkyl-$(C_3-C_8)$-cycloalkylthio" denotes, for example, the methylcyclopentylthio or methylcyclohexylthio group.

"$(C_1-C_4)$-Alkyl-$(C_4-C_8)$-cycloalkenylthio" denotes, for example, the methylcyclopentenylthio or methylcyclohexenylthio group.

"$(C_2-C_4)$-Alkenyl-$(C_3-C_8)$-cycloalkylthio" denotes, for example, the vinylcyclopentylthio, allylcyclopentylthio, vinylcyclohexylthio or allylcyclohexylthio group.

"$(C_2-C_6)$-Alkynyl-$(C_3-C_8)$-cycloalkylthio" denotes, for example, the ethynylcyclopentylthio, propargylcyclopentylthio, ethynylcyclohexylth io or propargylcyclohexylthio group.

"$(C_2-C_4)$-Alkenyl-$(C_4-C_8)$-cycloalkenylthio denotes, for example, the allylcyclopentenylthio or allylcyclohexenylthio group.

"$(C_1-C_8)$-Alkylsulfinyl" denotes, for example, the methyl-, ethyl-, propyl-, isopropyl-, butyl-, isobutyl-, sec-butyl-, tert-butyl- or octylsulfinyl group.

"$(C_3-C_8)$-Alkenylsulfinyl" denotes, for example, the allyl-, methylallyl-, butenyl- or octenylsulfinyl group.

"$(C_3-C_8)$-Alkynylsulfinyl" denotes, for example, the propargyl-, butynyl- or octinylsulfinyl group.

"$(C_3-C_{10})$-Cycloalkylsulfinyl" denotes a cycloalkylsulfinyl group whose hydrocarbon radical has the meaning given under the expression "$(C_3-C_{10})$-cycloalkyl".

"$(C_4-C_{10})$-Cycloalkenylsulfinyl" denotes a cycloalkenylsulfinyl group whose hydrocarbon radical has the meaning given under the expression "$(C_4-C_{10})$-cycloalkenyl".

"$(C_3-C_8)$-Cycloalkyl-$(C_1-C_4)$-alkylsulfinyl" denotes, for example, the cyclopropylmethylsulfinyl, cyclopropylethylsulfinyl, cyclopentylmethylsulfinyl or cyclohexylmethylsulfinyl group.

"$(C_4-C_8)$-Cycloalkenyl-$(C_1-C_4)$-alkylsulfinyl" denotes, for example, the cyclopentenylmethylsulfinyl or cyclohexenylmethylsulfinyl group.

"$(C_3-C_8)$-Cycloalkyl-$(C_3-C_4)$-alkenylsulfinyl" denotes, for example, the cyclopropylallylsulfinyl, cyclopentylallylsulfinyl or cyclohexylallylsulfinyl group.

"$(C_4-C_8)$-Cycloalkenyl-$(C_3-C_4)$-alkenylsulfinyl" denotes, for example, the cyclopentenylallylsulfinyl or cyclohexenylallylsulfinyl group.

"$(C_1-C_4)$-Alkyl-$(C_3-C_8)$-cycloalkylsulfinyl denotes, for example, the methylcyclopentylsulfinyl or methylcyclohexylsulfinyl group.

"$(C_1-C_8)$-Alkyl-$(C_4-C_8)$-cycloalkenylsulfinyl denotes, for example, the methylcyclopentenylsulfinyl or methylcyclohexenylsulfinyl group.

"$(C_2-C_4)$-Alkenyl-$(C_3-C_8)$-cycloalkylsulfinyl denotes, for example, the vinylcyclopentylsulfinyl, allylcyclopentylsulfinyl, vinylcyclohexylsulfinyl or allylcyclohexylsulfinyl group.

"($C_2$-$C_4$)-Alkynyl-($C_3$-$C_8$)-cycloalkylsulfinyl denotes, for example, the ethynylcyclopentylsulfinyl, propargylcyclopentylsulfinyl, ethynylcyclohexylsulfinyl or propargylcyclohexylsulfinyl group.

"($C_2$-$C_4$)-Alkenyl-($C_4$-$C_8$)-cycloalkenylsulfinyl denotes, for example, the vinylcyclopentenylsulfinyl, allylcyclopentenylsulfinyl, vinylcyclohexenylsulfinyl or allylcyclohexenylsulfinyl group.

"($C_1$-$C_{10}$)-Alkylsulfonyl" denotes, for example, the methyl-, ethyl-, propyl-, isopropyl-, butyl-, isobutyl-, sec-butyl-, tert-butyl- or octylsulfonyl group.

"($C_3$-$C_{10}$)-Alkenylsulfonyl" denotes, for example, the allyl-, methylallyl-, butenyl- or octenylsulfonyl group.

"($C_3$-$C_{10}$)-Alkynylsulfonyl" denotes, for example, the propargyl-, butynyl- or octynylsulfonyl group.

"($C_3$-$C_{10}$)-Cycloalkylsulfonyl" denotes a cycloalkylsulfonyl group whose hydrocarbon radical has the meaning given under the expression "($C_3$-$C_{10}$)-cycloalkyl".

"($C_4$-$C_{10}$)-Ccycloalkenylsulfonyl" denotes a cycloalkenylsulfonyl group whose hydrocarbon radical has the meaning given under the expression "($C_4$-$C_{10}$)-cycloalkenyl".

"($C_3$-$C_8$)-Cycloalkyl-($C_1$-$C_4$)-alkylsulfonyl" denotes, for example, the cyclopropylmethylsulfonyl, cyclopropylethylsulfonyl, cyclopentylmethylsulfonyl or cyclohexylmethylsulfonyl group.

"($C_4$-$C_8$)-Cycloalkenyl-($C_1$-$C_4$)-alkylsulfonyl" denotes, for example, the cyclopentenylmethylsulfonyl or cyclohexenylmethylsulfonyl group.

"($C_3$-$C_8$)-Cycloalkyl-($C_3$-$C_4$)-alkenylsulfonyl" denotes, for example, the cyclopropylallylsulfonyl, cyclopentylallylsulfonyl or cyclohexylallylsulfonyl group.

"($C_4$-$C_8$)-Cycloalkenyl-($C_3$-$C_4$)-alkenylsulfonyl" denotes, for example, the cyclopentenylallylsulfonyl or cyclohexenylallylsulfonyl group.

"($C_1$-$C_4$)-Alkyl-($C_3$-$C_8$)-cycloalkylsulfonyl" denotes, for example, the methylcyclopentylsulfonyl or methylcyclohexylsulfonyl group.

"($C_1$-$C_4$)-Alkyl-($C_4$-$C_8$)-cycloalkenylsulfonyl" denotes, for example, the methylcyclopentenylsulfonyl or methylcyclohexenylsulfonyl group.

"($C_2$-$C_4$)-Alkenyl-($C_3$-$C_8$)-cycloalkylsulfonyl" denotes, for example, the vinylcyclopentylsulfonyl, allylcyclopentylsulfonyl, vinylcyclohexylsulfonyl or allylcyclohexylsulfonyl group.

"($C_2$-$C_4$)-Alkynyl-($C_3$-$C_8$)-cycloalkylsulfonyl" denotes, for example, the ethynylcyclopentylsulfonyl, propargylcyclopentylsulfonyl, ethynylcyclohexylsulfonyl or propargylcyclohexylsulfonyl group.

"($C_2$-$C_4$)-Alkenyl-($C_4$-$C_8$)-cycloalkenylsulfonyl" denotes, for example, the vinylcyclopentenylsulfonyl, allylcyclopentenylsulfonyl, vinylcyclohexenylsulfonyl or allylcyclohexenylsulfonyl group.

"($C_1$-$C_{10}$)-Alkylamino" denotes a nitrogen atom which is substituted by one or two identical or different alkyl radicals of the above definition.

"($C_3$-$C_{10}$)-Alkenylamino" denotes a nitrogen atom which is substituted by one or two identical or different alkenyl radicals of the above definition.

"($C_3$-$C_{10}$)-Alkynylamino" denotes a nitrogen atom which is substituted by one or two identical or different alkynyl radicals of the above definition.

"($C_3$-$C_8$)-Cycloalkylamino" denotes a nitrogen atom which is substituted by one or two identical or different cycloalkyl radicals of the above definition.

"($C_3$-$C_8$)-Cycloalkyl-($C_1$-$C_4$)-alkylamino" denotes, for example, the cyclopropylmethylamino, cyclopropylethylamino, cyclopentylmethylamino or cyclohexylmethyamino group.

"($C_4$-$C_8$)-Cycloalkenyl-($C_1$-$C_4$)-alkylamino" denotes, for example, the cyclopentenylmethylamino or cyclohexenylmethylamino group.

"($C_3$-$C_8$)-Cycloalkyl-($C_3$-$C_4$)-alkenylamino" denotes, for example, the cyclopropylallylamino, cyclopentylallylamino or cyclohexylallylamino group.

"($C_4$-$C_8$)-Cycloalkenyl-($C_3$-$C_4$)-alkenylamino" denotes, for example, the cyclopentenylallylamino or cyclohexenylallylamino group.

"($C_1$-$C_4$)-Alkyl-($C_3$-$C_8$)-cycloalkylamino" denotes, for example, the methylcyclopentylamino or methylcyclohexylamino group.

"($C_1$-$C_8$)-Alkyl-($C_4$-$C_8$)-cycloalkenylamino" denotes, for example, the methylcyclopentenylamino or methylcyclohexenylamino group.

"($C_2$-$C_4$)-Alkenyl-($C_3$-$C_8$)-cycloalkylamino" denotes, for example, the vinylcyclopentylamino, allylcyclopentylamino, vinylcyclohexylamino or allylcyclohexylamino group.

"($C_2$-$C_4$)-Alkynyl-($C_3$-$C_8$)-cycloalkylamino" denotes, for example, the ethynylcyclopentylamino, propargylcyclopentylamino, ethynylcyclohexylamino or propargylcyclohexylamino group.

"($C_2$-$C_4$)-Alkenyl-($C_4$-$C_8$)-cycloalkenylamino" denotes, for example, the vinylcyclopentenylamino, allylcyclopentenylamino, vinylcyclohexenylamino or allylcyclohexenylamino group.

Also included, in addition to mono-N-substituted amino groups, are the corresponding N,N-disubstituted derivatives, in particular derivatives in which one hydrogen is replaced by one ($C_1$-$C_4$)-alkyl group.

The expression "($C_1$-$C_{10}$)-trialkylsilyl" denotes a silicon atom which carries three identical or different alkyl radicals according to the above definition. Analogously, "aryl-($C_1$-$C_6$)-dialkylsilyl" denotes a silicon atom which carries one aryl radical and two identical or different alkyl radicals according to the above definition, "diaryl-($C_1$-$C_6$)-alkylsilyl" denotes a silicon atom which carries one alkyl radical and two identical or different aryl radicals according to the above definition, and "triarylsilyl" denotes a silicon atom which carries three identical or different aryl radicals according to the above definition.

The expression "aryl" is to be understood as meaning a carbocyclic, i.e. constructed of carbon atoms, aromatic radical having preferably 6 to 14, in particular 6 to 12, carbon atoms, such as, for example, phenyl, naphthyl or biphenylyl, preferably phenyl.

"Aroyl" accordingly denotes an aryl radical as defined above which is attached via a carbonyl group, such as, for example, the benzoyl group.

The expression "four- to eight-membered aliphatic heterocycle containing at least one oxygen, sulfur, nitrogen and/or silicon ring atom" denotes a cyclic radical which may be fully saturated or partially unsaturated, but not aromatic, and which is interrupted by one or more, preferably one or two, identical or different atoms from the group consisting of nitrogen, sulfur, oxygen and silicon, where, however, two oxygen atoms may not be directly adjacent. The heterocycle has four to eight ring atoms which, in addition to the heteroatoms mentioned above, are carbon atoms. The expression "heterocyclyl" preferably denotes a cyclic radical which can be completely saturated, partially unsaturated or completely unsaturated and which can be interrupted by at least one or more, preferably one to three, identical or different atoms selected from the group consisting of nitrogen, sulfur and oxygen, where, however, two oxygen atoms may not be directly adjacent and at least one carbon atom has to be present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, isoxzolidine or thiazolidine radical. Accordingly, the expression "heteroaromatic" embraces, from among the meanings mentioned above under "heterocyclyl", in each case the completely unsaturated aromatic heterocyclic compounds.

Heterocyclyl particularly preferably denotes a saturated, partially saturated or aromatic ring system having 3 to 6 ring members and 1 to 4 heteroatoms selected from the group consisting of O, S and N, where at least one carbon atom has to be present in the ring.

Very particularly preferably, heterocyclyl denotes a pyridine, pyrimidine, 1,2,4-oxadiazole, 1,3,4-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane and oxetane radical.

"Aryloxy" accordingly denotes an aryl radical as defined above which is attached via an oxygen atom, such as, for example, the phenoxy or naphthyloxy group.

"Arylthio" denotes an aryl radical which is attached via a sulfur atom, for example the phenylthio or the 1- or 2-naphthylthio radical.

"Arylamino" denotes an aryl radical which is attached via a nitrogen atom, for example the anilino or the 1- or 2-naphthamino radical.

"N-($C_1$-$C_4$)-alkyl-arylamino" denotes, for example, the N-methyl- or N-ethylanilino radical.

"Aryl-($C_1$-$C_4$)-alkoxy" denotes an aryl radical which is attached via a ($C_1$-$C_4$)-alkoxy group, for example the benzyloxy, phenylethoxy, phenylbutoxy or naphthylmethoxy radical.

"Aryl-($C_3$-$C_4$)-alkenyloxy" denotes an aryl radical which is attached via a ($C_3$-$C_4$)-alkenyloxy group, for example the 1-, 2-, or 3-phenylallyloxy radical.

"Aryl-($C_1$-$C_4$)-alkylthio" denotes an aryl radical which is attached via an alkylthio radical, for example the benzylthio, naphthylmethylthio or the 1- or 2-phenylethylthio radical.

"Aryl-($C_3$-$C_4$)-alkenylthio" denotes an aryl radical which is attached via a ($C_3$-$C_4$)-alkenylthio group, for example the 1,-2- or 3-phenylallylthio radical.

"Aryl-($C_3$-$C_4$)-alkenylamino" denotes an aryl radical which is attached via a ($C_3$-$C_4$)-alkenylamino group, for example the 1,-2- or 3-phenylallylamino radical.

"Aryl-($C_1$-$C_8$)-dialkylsilyl" denotes, for example, a phenyl- or naphthyldimethylsilyl group.

"Diaryl-($C_3$-$C_4$)-alkylsilyl" denotes, for example, a diphenyl-, phenylnaphthyl- or dinaphthylmethylsilyl group.

"Triarylsilyl" denotes, for example, a triphenyl-, diphenylnaphthyl- or trinaphthylsilyl group.

Furthermore, the expression that "if appropriate in all groups mentioned for $R^5$, $R^6$, $R^7$, $R^8$, $R^9$, $R^{10}$ and $R^{11}$, one to three hydrogens attached to carbon may be replaced by halogen atoms, in the case of fluorine also up to the maximum number" includes, for example, the following radicals:

haloalkyl, such as, for example, the 1- or 2-fluoroethyl, the trifluoromethyl, the 2,2,2-trifluoroethyl-, the chloromethyl, the fluoromethyl, the difluoromethyl or the 1,1,2,2-tetrafluoroethyl group;

haloalkenyl, such as, for example, the 1-, 2- or 3-fluoroallyl group or the 1,1-difluoropropen-3-yl group;

haloalkoxy, such as, for example, trifluoromethoxy or 2,2,2-trifluoroethoxy;

haloalkylthio, such as, for example, trifluoromethylthio;

haloalkylsulfinyl, such as, for example, trifluoromethylsulfinyl;

haloalkylsulfonyl, such as, for example, trifluoromethylsulfonyl;

halocyclopropyl, such as, for example, 1,1-difluorocycloprop-2-yl.

Depending on the nature of the substituents defined above, the compounds of the formula (I) have acidic or basic properties and are capable of forming salts. If, for example, the compounds of the formula (I) carry groups such as hydroxyl, carboxyl or other groups which induce acidic properties, these compounds can be reacted with bases to form salts. Suitable bases are, for example, hydroxides, carbonates and bicarbonates of the alkali metals and alkaline earth metals, in particular those of sodium, potassium, magnesium and calcium, furthermore ammonia, primary, secondary and tertiary amines with ($C_1$-$C_4$)-alkyl radicals and mono-, di- and trialkanolamines of ($C_1$-$C_4$)-alkanols. If, for example, the compounds of the formula (I) carry groups such as amino, alkylamino or other groups which induce basic properties, these compounds can be reacted with acids to form salts. Suitable acids are, for example, mineral acids, such as hydrochloric, sulfuric and phosphoric acid, organic acids, such as acetic acid or oxalic acid, and acidic salts, such as $NaHSO_4$ and $KHSO_4$. The salts obtainable in this manner likewise have insecticidal, acaricidal and miticidal properties.

The compounds of the formula (I) can have one or more asymmetric carbon atoms or stereoisomers on double bonds. Therefore, it is possible for enantiomers or diastereomers to be present. The invention embraces both the pure isomers and their mixtures. The mixtures of diastereomers can be separated into the isomers by customary methods, for example by selective crystallization from suitable solvents or by chromatography. Racemates can be separated into the enantiomers by customary methods.

The preparation of the compounds according to the invention is carried out by methods known per se from the literature, as described in standard works on organic synthesis (cf., for example, Houben-Weyl, Methoden der Organischen Chemie [Methods of Organic Chemistry], Georg-Thieme-Verlag, Stuttgart).

The preparation is carried out under reaction conditions which are known and are suitable for the reactions mentioned. It is also possible to use variants which are known per se but not mentioned here in detail.

If desired, the starting materials can also be formed in situ, i.e. they are not isolated from the reaction mixture but immediately reacted further to give the compounds of the formula (I).

The present invention also relates to processes for preparing compounds of the formula (I).

To prepare compounds of the formula (I) in which $R^1$, $R^2$, $R^3$, $R^4$, $R^5$, A, Y and n have the meanings given for formula (I), for example, a carboxylic acid of the formula (III),

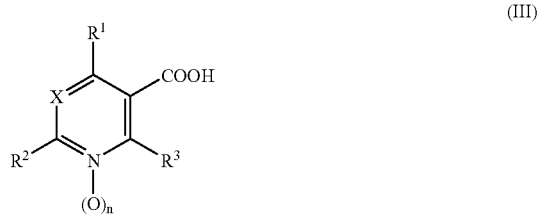

(III)

in which X, $R^1$, $R^2$, $R^3$ and n have the meanings given above for formula (I) is, for example, in the form of an activated derivative of this acid, for example an acid halide, ester or anhydride, reacted in the presence of a base, preferably at least one amine, such as triethylamine, diisopropylethylamine, pyridine or lutidine, alkali metal carbonate, alkali metal bicarbonate or alkali metal hydroxide, or of combinations of these compounds, with a compound of the formula (IV), in which $R^4$ and $R^5$ have the meanings given above for formula (I)

$HNR^4R^5$ (IV), and the radical $R^5$ is subsequently, if appropriate, derivatized further.

Collections of compounds of the formula (I) which can be synthesized by the abovementioned scheme may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany or Radleys, Shirehill, Saffron Walden, Essex, England, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries.

The present invention also relates to libraries which comprise at least two compounds of the formula (I).

The compounds of the formula (I) are suitable for controlling animal pests, in particular insects, arachnids, helminths and mollusks, very especially preferably for controlling insects and arachnids which are encountered in agriculture, in livestock breeding, in forests, in the protection of stored goods and materials, and in the hygiene sector, and have good plant tolerance and favorable toxicity to warm-blooded species. They are active against normally sensitive and resistant species and against all or individual developmental stages. The abovementioned pests include:

From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Eotetranychus* spp., *Oligonychus* spp., *Eutetranychus* spp. From the order of the Isopoda, for example, *Oniscus aselus, Armadium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis, Schistocerca gregaria.*

From the order of the Isoptera, for example, *Reticulitermes* spp.

From the order of the Anoplura, for example, *Phylloera vastatrix, Pemphigus* spp., *Pediculus humanus corporis, Haematopinus* spp., *Linognathus* spp.

From the order of the Mallophaga, for example, *Trichodectes* pp., *Damalinea* spp.

From the order of the Thysanoptera, for example, *Hercinothrips femoralis, Thrips tabaci*.

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylloides chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrynchus assimilis, Hypera postica, Dermestes* spp., *Trogoderma, Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica*.

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hypobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa*.

From the order of the Siphonaptera, for example, *Xenopsylla cheopsis, Ceratophyllus* spp.

From the order of the Arachnida, for example, *Scorpio maurus, Latrodectus mactans*.

From the class of the helminths, for example, *Haemonchus, Trichostrongulus, Ostertagia, Cooperia, Chabertia, Strongyloides, Oesophagostomum, Hyostrongulus, Ancylostoma, Ascaris* and *Heterakis* and also *Fasciola*.

From the class of the Gastropoda, for example, *Deroceras* spp., *Arion* spp., *Lymnaea* spp., *Galba* spp., *Succinea* spp., *Biomphalaria* spp., *Bulinus* spp., *Oncomelania* spp.

From the class of the Bivalva, for example, *Dreissena* spp.

It is furthermore possible to control protozoa such as *Eimeria*.

The plant-parasitic nematodes which can be controlled in accordance with the invention include, for example, the root-parasitic soil-dwelling nematodes such as, for example, those of the genera *Meloidogyne* (root knot nematodes, such as *Meloidogyne incognita, Meloidogyne hapla* and *Meloidogyne javanica*), *Heterodera* and *Globodera* (cyst-forming nematodes, such as *Globodera rostochiensis, Globodera pallida, Heterodera trifolii*) and of the genera *Radopholus*, such as *Radopholus similis, Pratylenchus* such as *Pratylenchus neglectus, Pratylenchus penetrans* and *Pratylenchus curvitatus;*

*Tylenchulus* such as *Tylenchulus semipenetrans, Tylenchorhynchus*, such as *Tylenchorhynchus dubius* and *Tylenchorhynchus claytoni, Rotylenchus* such as *Rotylenchus robustus, Heliocotylenchus* such as *Haliocotylenchus multicinctus, Belonoaimus* such as *Belonoaimus longicaudatus, Longidorus* such as *Longidorus elongatus, Trichodorus* such as *Trichodorus primitivus* and *Xiphinema* such as *Xiphinema index*.

Other nematode genera which can be controlled using the compounds according to the invention are *Ditylenchus* (stem parasites, such as *Ditylenchus dipsaci* and *Ditylenchus destructor*), *Aphelenchoides* (foliar nematodes, such as *Aphelenchoides ritzemabosi*) and *Anguina* (seed nematodes, such as *Anguina tritici*).

The invention also relates to compositions, for example crop protection compositions, preferably insecticidal, acaricidal, ixodicidal, nematicidal, molluscicidal or fungicidal, especially preferably insecticidal and acaricidal, compositions which comprise one or more compounds of the formula (I) in addition to suitable formulation auxiliaries.

To prepare the compositions according to the invention, the active substance and the other additives are combined and brought into a suitable use form.

The invention also relates to compositions, in particular insecticidal and acaricidal compositions, which comprise the compounds of the formula (I) in addition to suitable formulation auxiliaries.

In general, the compositions according to the invention comprise 1 to 95% by weight of the active substances of the formula (I). They can be formulated in various ways, depending on the biological and/or chemical-physical parameters which prevail. The following are examples of possible formulations:

Wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulations are known in principle and are described, for example, in: Winnacker-Küchler, "Chemische Technologie" [Chemical Technology], Volume 7, C. Hanser Verlag Munich, 4th Edition 1986; van Falkenberg, "Pesticides Formulations", Marcel Dekker N.Y., 2nd Ed. 1972-73; K. Martens, "Spray Drying Handbook", 3rd Ed. 1979, G. Goodwin Ltd. London.

The necessary formulation auxiliaries i.e. carrier materials and/or surface active substances such as inert materials, surfactants, solvents and other additives, are also known and described, for example, in: Watkins, "Handbook of Insecticide Dust Diluents and Carriers", 2nd Ed., Darland Books, Caldwell N. J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active ethylene oxide adducts] Wiss. Verlagsgesell., Stuttgart 1967; Winnacker-Küchler, "Chemische Technologie", Volume 7, C. Hanser Verlag Munich, 4th Edition 1986.

Based on these formulations, it is also possible to prepare combinations with other pesticidally active materials, fertilizers and/or growth regulators, for example in the form of a ready-mix formulation or a tank mix. Wettable powders are preparations which are uniformly dispersible in water which, besides the active substance, also comprise wetters, for example polyoxyethylated alkylphenols, polyoxyethylated fatty alcohols, alkylsulfonates or alkylphenolsulfonates and dispersants, for example sodium lignosulfonate or sodium 2,2'-dinaphthylmethane-6,6'-disulfonate, in addition to a diluent or inert material.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. As emulsifiers, the following can be used, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained, for example, by grinding the active substance with finely divided solid materials, for example talc or natural clays, such as kaolin, bentonite, pyrophyllite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or else mineral oils. Suitable active substances can also be granulated in the manner which is customary for the preparation of fertilizer granules, if desired as a mixture with fertilizers.

The active substance concentration in wettable powders is, for example, approximately 10 to 90% by weight, the remainder to 100% by weight is composed of customary formulation auxiliaries. In the case of emulsifiable concentrates, the active substance concentration may be approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

In addition, the abovementioned active substance formulations comprise, if appropriate, the tackifiers, wetters, dispersants, emulsifiers, penetrants, solvents, fillers or carriers which are conventional in each case.

For use, the concentrates, which are present in commercially available form, are, if desired, diluted in the customary manner, for example in the case of wettable powders, emulsifiable concentrates, dispersions and in some cases also microgranules, using water. Preparations in the form of dusts and granules and sprayable solutions are usually not diluted any further with other inert substances prior to use.

The application rate required varies with the external conditions such as, inter alia, temperature and humidity. It may vary within wide limits, for example between 0.0005 and 10.0 kg/ha or more of active substance, but it is preferably between 0.001 and 5 kg/ha of active compound.

The active substances according to the invention, in their commercially available formulations and in the use forms prepared from these formulations may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Preferred components in mixtures are:

1. from the group of the phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;

2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl)carbamate, oxamyl, pirimicarb, propoxur, thiodicarb, thiofanox, 1-methylthio(ethylideneamino)-N-methyl-N-(morpholinothio)carbamate (UC 51717), triazamate;

3. from the group of the carboxylic esters acrinathrin, allethrin, alphametrin, 5-benzyl-3-furylmethyl(E)-(1R)-cis-2,2-dimethyl-3-(2-oxothiolan-3-ylidenemethyl)cyclopropanecarboxylate, beta-cyfluthrin, beta-cypermethrin, bioallethrin, bioallethrin((S)-cyclopentylisomer), bioresmethrin, bifenthrin, (RS)-1-cyano-1-(6-phenoxy-2-pyridyl)methyl(1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flubrocythrinate flucythrinate, flumethrin, fluvalinate (D isomer), imiprothrin (S-41311), lambda-cyhalothrin, permethrin, phenothrin ((R) isomer), prallethrin, pyrethrins (natural products), resmethrin, tefluthrin, tetramethrin, theta-cypermethrin (TD-2344), tralomethrin, trans-fluthrin, zeta-cypermethrin (F-56701);

4. from the group of the amidines amitraz, chlordimeform;
5. from the group of the tin compounds cyhexatin, fenbutatin oxide;
6. others abamectin, ABG-9008, acequinocyl, azadirachtin, acetamiprid, *Anagrapha falcitera*, AKD-1022, AKD- 3059, AKD-3088, AL-9811, ANS-118, *Bacillus thuringiensis, Beauveria bassianea*, bensultap, bifenazate (D-2341), binapacryl, BJL-932, bromopropylate, BAJ-2740 (spirodiclofen), BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chloroxyfen, clothianidine, chromafenozide (ANS-118), A-184699, 2-naphthylmethyl cyclopropanecarboxylate (Ro12-0470), cyromazin, CM-002x, DBI-3204, diacloden (thiamethoxam), diafenthiuron, ethyl 2-chloro-N-(3,5-dichloro-4-(1,1,2,3,3,3-hexafluoro-1-propyloxy)phenyl)-carbamoyl)-2-carboximidate, DDT, dicofol, diflubenzuron, N-(2,3-dihydro-3-methyl-1,3-thiazol-2-ylidene)-2,4-xylidine, dinobuton, dinocap, diofenolan, DPX-062, emamectin benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl) diphenyl ether (MTI 800), granulosis and nuclear polyhedrosis viruses, fenpyroximate, fenthiocarb, fluacrypyrim, flufenzine, flubenzimine, flucycloxuron, flufenoxuron, flufenprox (ICI-A5683), fluproxyfen, FMC-F6028, gamma-HCH, halofenozide (RH-0345), halofenprox (MTI-732), hexaflumuron (DE__473), hexythiazox, HOI-9004, hydramethylnon (AC 217300), lufenuron, imidacloprid, indoxacarb (DPX-MP062), kanemite (AKD-2023), M-020, MTI-446, ivermectin, M-020, IKA-2000, IKI-220, MKI-245, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), NC-196, NNI-0001, nidintefuran, pyriproxyfen (S-71639), pirydaryl, protrifenbute, pyriproxy-fen, NC-196, NC-1111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, thiamethoxam, TI-435, tolfenpyrad (OMI-88), triazamate (RH-7988), triflumuron, verbutin, vertalec (Mykotal), YI-5301 and Yi-6101.

The abovementioned components for combinations are known active substances, many of which are described in Ch. R Worthing, S. B. Walker, The Pesticide Manual, 12th Edition, British Crop Protection Council Farnham, 2000.

The following products, for example, may be mentioned as fungicides suitable for combination with the compounds of formula (I) according to the invention:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazot, fenarimol, fenfuram, fenpiclonil, fenpropidin, fenpropimorph, fentinacetate, fentinhydroxide, ferimzone (TF164), fluazinam, fluobenzimine, fluquinconazole, fluoromide, flusilazole, flutolanil, fluthafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as Cu oxychloride, oxine-Cu, Cu oxide, mancozeb, maneb, mepanipyrim (KIF 3535), metconazole, mepronil, metalaxyl, methasulfocarb, methfuroxam, MON 24000, myclobutanil, nabam, nitrothalido-propyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizole, triforine, validamycin, vinchlozolin, XRD 563, zineb, sodium dodecylsulfonate, sodium dodecylsulfate, sodium C13/C15-alcohol ether sulfonate, sodium cetostearyl phosphate ester, dioctyl sodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropheneamines, laurylpyrimidinium bromide, ethoxylated quarternized fatty amines, alkyldimethylbenzylammonium chloride and 1-hydroxylethyl-2-alkylimidazoline.

The active substance content of the use forms prepared from the commercially available formulations may range from 0.00000001 up to 95% by weight of active substance, preferably between 0.00001 and 1% by weight.

Application is effected in a customary manner adapted to suit the use forms.

Accordingly, in a further aspect of the invention there is provided the use of a compound of the formula (I) or a salt thereof for controlling harmful insects, acarids and/or nematodes. In a further aspect of the invention there is provided a method for controlling harmful insects, acarids and/or nematodes which comprises applying an effective amount of a compound of the formula (I) or a salt thereof to these pests, or to the plants, areas or substrates infested with them.

The active substances according to the invention are also suitable for controlling endoparasites and ectoparasites in the human and veterinary medicine sector and/or in the field of animal keeping. The active substances according to the invention are applied in the known manner, such as by oral administration in the form of, for example, tablets, capsules, drinks or granules, by dermal application in the form of, for example, dipping, spraying, pouring on and spotting on, and dusting, and by parenteral administration in the form of, for example, an injection.

Accordingly, the invention also provides the use of a compound of the formula (I) or a salt thereof for preparing a pharmaceutical for use in humans and/or animals, preferably a veterinary pharmaceutical, especially for the control of ecto- and/or endoparasites.

Accordingly, the compounds of the formula (I) according to the invention can also be employed particularly advantageously for treating warm-blooded animals, in particular in livestock keeping (for example cattle, sheep, pigs and poultry such as chickens, geese and the like). In a preferred embodiment of the invention, the compounds, if appropriate in suitable formulations, are administered orally to the animals, if appropriate together with the drinking water or feed. Since excretion in the feces is efficient, the development of insects in the animals' feces can be prevented very easily in this manner. The dosages and formulations which are suitable in each case depend, in particular, on the species and the developmental stage of the productive livestock and also on the risk of infestation and can be determined readily and established by customary methods. For example, the compounds can be employed in cattle at dosages of 0.01 to 1 mg/kg bodyweight.

In addition to their lethal effect on pests, the compounds of the formula (I) also have a pronounced repellent effect.

A repellent for the purpose of the invention is a substance or substance mixture which has a warding-off or fending-off effect on other life organisms, in particular harmful pests and nuisance pests. The term also encompasses effects such as the antifeeding effect, where the intake of feed is disturbed or prevented (antifeedant effect), supression of oviposition, or an effect on the development of the population.

The invention therefore also provides the use of compounds of the formula (I) or their salts for achieving the abovementioned effects, in particular in the case of the pests stated in the biological examples.

The invention also provides a method for fending off, or warding off, harmful organisms, where one or more compounds of the formula (I) or their salts are applied to the site from which the harmful organisms are to be fended off or warded off.

In the case of a plant, application may mean, for example, a treatment of the plant, or also of the seed.

As regards the effect on populations, it is interesting to note that effects can also be observed in succession during the development of a population, where summation may take place. In such a case, the individual effect itself may only have an efficacy of markedly less than 100% but in total an efficacy of 100% is still achieved in the end.

Moreover, the compounds of the formula (I) or their salts are distinguished by the fact that the composition is usually applied earlier than in the case of a direct control, if the abovementioned effects are to be exploited. The effect frequently lasts over a long period, so that a duration of action of over 2 months is achieved.

The effects are observed in insects, arachnids and others of the above mentioned pests.

In addition to the abovementioned application methods, the active compounds of the formula (I) according to the invention have excellent systemic action. Accordingly, the active compounds can also be introduced into the plants via parts of the plant, both below ground and above ground (for example root, stem, leaf), if the active compounds are applied, in liquid or solid form, onto the plant and/or in the direct vicinity of the plant (for example granules in soil application, application in flooded rice paddies).

Furthermore, the active compounds according to the invention are particularly useful for the treatment of vegetative and generative plant propagation material, such as, for example, of seeds, for example of cereals, vegetables, cotton, rice, sugar beet and other crops and ornamental plants, of bulbs, seedlings and tubers of other crops and ornamental plants which are propagated vegetatively. The treatment can be carried out before sowing or before planting (for example by special seed coating techniques, by dressing in liquid or solid form or as a seed box treatment), during sowing or planting or after sowing or planting by special application techniques (for example furrow treatment). The amount of active compound used can vary within a relatively large range, depending on the application. In general, the application rates are between 1 g and 10 kg of active compound per hectare of soil surface.

The compounds of the formula (I) can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore provides the use of compounds of the formula (I) for controlling harmful organisms in transgenic crop plants.

The use of the compounds according to the invention embraces, in addition to direct application onto the pests, any other application in which compounds of the formula (I) act on the pests. Such indirect applications can, for example, be the use of compounds which, for example in the soil, the plant or the pest, decompose into compounds of the formula (I) or are degraded into compounds of the formula (I).

The contents of the German patent application 10148290.6, whose priority is claimed by the present application, and of the enclosed abstract is expressly referred to; by way of reference, it is incorporated into this description.

The examples below serve to illustrate the invention without limiting it.

A. CHEMICAL EXAMPLES

Example A

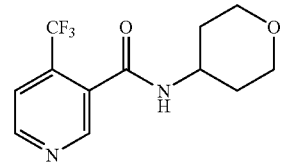

N-(Tetrahydropyran-4-yl)-4-trifluoromethylnicotinamide

At 0° C., a solution of 0.63 g (3.0 mmol) of 4-trifluoronicotinoyl chloride in a little dichloromethane was added dropwise to a solution of 0.30 g (3.0 mmol) of 4-aminotetrahydropyran (prepared by reductive amination of tetrahydropyran-4-one; $NH_3/H_2/Ni$, 100 bar, 50° C.) and 0.35 g (3.5 mmol) of triethylamine in 25 ml of dichloromethane. The mixture was stirred at room temperature for another two hours, saturated sodium chloride solution was added and the phases were separated. The aqueous phase was extracted two more times with dichloromethane. The combined organic phases were dried and concentrated. This gave 0.46 g (67.8% of theory) of product as a colorless solid of melting point 149-150° C.

Example B

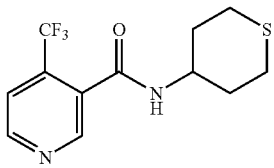

N-(Tetrahydrothiopyran-4-yl)-4-trifluoromethylnicotinamide

Analogously to Example A, equimolar amounts of 4-aminotetrahydrothiopyran (prepared from tetrahydrothiopyran-4-one via the corresponding oxime and subsequent reduction with lithium aluminum hydride in tetrahydrofuran) and 4-trifluoromethylnicotinoyl chloride were reacted in the presence of triethylamine. This gave, after silica gel chromatography (ethyl acetate), the amide as a colorless solid of melting point 161-163° C. (Yield 51.3% of theory).

Example C

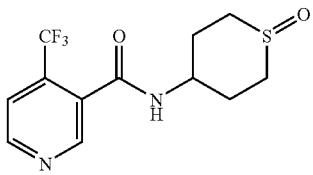

N-(Tetrahydrothiopyran-4-yl)-4-trifluoromethylnicotinamide S-oxide

At 0° C., a solution of 1.23 g (5 mmol) of 70% strength 3-chloroperbenzoic acid in 25 ml of dichloromethane was added dropwise to a solution of 1.45 g (5 mmol) of N-(tetrahydrothiopyran-4-yl)-4-trifluoromethylnicotinamide (Example B) in 50 ml of dichloromethane. The mixture was stirred at room temperature for 6 hours and then extracted with sodium carbonate solution, and the organic phase was dried. Concentration gave a colorless oil which crystallized after trituration with ethyl acetate. Filtration with suction gave 1.0 g (65.3% of theory) of product of melting point 243-244° C.

Example D

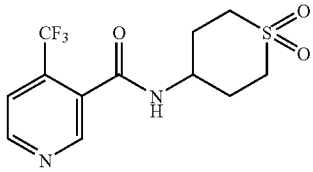

N-(Tetrahydrothiopyran-4-yl)-4-trifluoromethylnicotinamide S,S-dioxide

At 0° C., a solution of 2.46 g (10 mmol) of 70% strength 3-chloroperbenzoic acid in 50 ml of dichloromethane was added dropwise to a solution of 1.45 g (5 mmol) of N-(tetrahydrothiopyran-4-yl)-4-trifluormethylnicotinamide (Example B) in 50 ml of dichloromethane. The mixture was stirred at room temperature for 6 hours and extracted with sodium carbonate solution, and the organic phase was dried. Concentration gave a colorless oil which crystallized after trituration with ethyl acetate. Filtration with suction gave 1.3 g (80.7% of theory) of product of melting point 248° C. (decomposition).

Example E

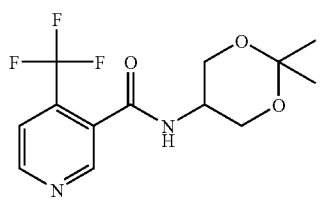

N-(2,2-Dimethyl-1,3-dioxa-cyclohexyl)-4-trifluoromethylnicotinamide

In the presence of 0.50 g of p-toluolsulfonic acid hydrate, 2.64 g (10 mmol) of N-(4-trifluoromethylnicotinoyl)serinol and 4.20 g (40 mmol) of acetone dimethyl acetal in 50 ml of toluene were stirred at 80° C. for 12 hours, with distillative removal of the methanol that was formed. After cooling, the mixture was extracted with dilute sodium hydroxide solution and water and the organic phase was dried and concentrated. This gave 1.5 g of product (49.3% of theory) as a colorless solid of melting point 155-156° C.

Preparation of the Starting Material N-(4-trifluoromethylnicotinoyl)serinol

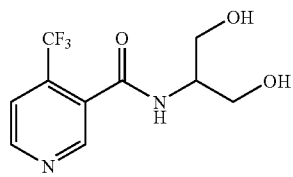

3.9 g (20 mmol) of 4-trifluoromethylnicotinic acid and 3.2 g (20 mmol) of carbonyl diimidazole in 100 ml of dry tetrahydrofuran were stirred at 40-50° C. for 6 hours. After cooling, 1.8 g (20 mmol) of serinol were added, and stirring was continued at 50-60° C. for another 4 hours. The crude product obtained after removal of the solvent under reduced pressure was purified by silica gel chromatography. This gave 2.9 g of product (55.3% of theory) of melting point 155-156° C.

The compounds listed in the tables below can be prepared in an analogous manner.

TABLE 1

Structure: 4-(trifluoromethyl)pyridine-3-carboxamide with NR⁴R⁵ group (pyridine N at position 1, CF₃ at position 4, C(O)NR⁴R⁵ at position 3)

| Ex. No. | NR⁴R⁵ | m.p.[° C.] |
|---|---|---|
| 1 | NH-oxetan-3-yl | |
| 2 | NH-(tetrahydrofuran-3-yl) | |
| 3 | NH-(2-methyltetrahydrofuran-3-yl) | oil |
| 4 | NH-(5-methyltetrahydrofuran-3-yl) | |
| 4 | NH-(4-methyltetrahydrofuran-3-yl) | |
| 5 | NH-(4,4-dimethyltetrahydrofuran-3-yl) | |
| 6 | NH-(5,5-dimethyltetrahydrofuran-3-yl) | |
| 7 | NH-(2,2-dimethyltetrahydrofuran-3-yl) | |
| 8 | NH-(2-oxotetrahydrofuran-3-yl) | 121-122 |

TABLE 1-continued

| Ex. No. | NR⁴R⁵ | m.p.[° C.] |
|---|---|---|
| 9 | NH-(4-methyl-2-oxotetrahydrofuran-3-yl) | |
| 9 | NH-(4-methyl-2-oxotetrahydrofuran-3-yl) | 168-171 |
| 9 | NH-(4,4-dimethyl-2-oxotetrahydrofuran-3-yl) | 119-121 |
| 10 | NH-(5-methyl-2-oxotetrahydrofuran-3-yl) | 140-142 |
| 11 | NH-(5,5-dimethyl-2-oxotetrahydrofuran-3-yl) | 83-84 |
| 12 | NH-(2-oxotetrahydrofuran-4-yl) | |
| 13 | NH-(5-methyl-2-oxotetrahydrofuran-4-yl) | |
| 14 | NH-(3-methyl-2-oxotetrahydrofuran-4-yl) | |

TABLE 1-continued
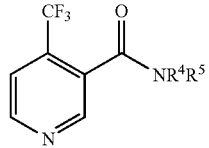
| Ex. No. | NR⁴R⁵ | m.p.[° C.] |
|---|---|---|
| 15 | 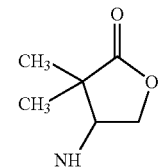 | |
| 16 | 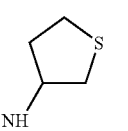 | |
| 17 | 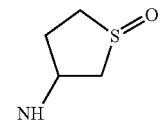 | 78–80 |
| 18 | 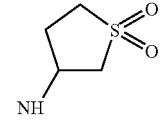 | 153–154 |
| 19 | 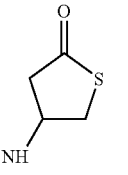 | 168–169 |
| 20 | 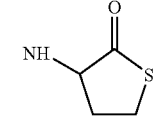 | |
| 21 | 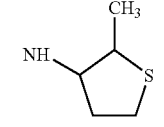 | 151–153 |
| 22 | 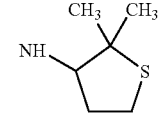 | 112–116 (isomer mixtures) |
| 23 | 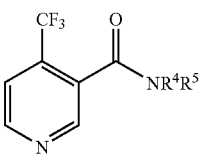 | oil |
TABLE 1-continued
| Ex. No. | NR⁴R⁵ | m.p.[° C.] |
|---|---|---|
| 24 | 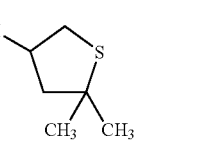 | 118–121 |
| 25 | 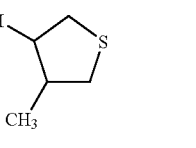 | oil |
| 26 | 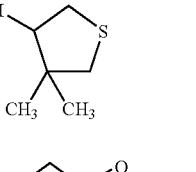 | cis isomer: oil<br>trans isomer: oil |
| 27 | 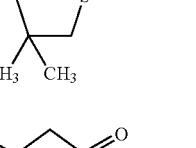 | |
| 28 | 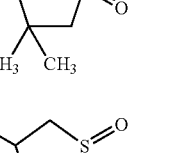 | |
| 29 | 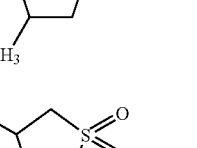 | |
| 30 | 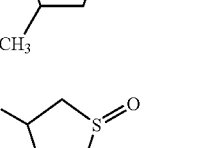 | cis-aminomethyl: oil<br>trans-aminomethyl: 105–108 |
| 31 | 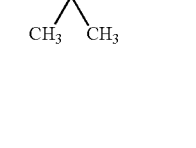 | |
| 32 | | |

TABLE 1-continued

3-CF3, 4-H pyridine-carboxamide NR⁴R⁵ (left); 4-CF3, 3-H pyridine-carboxamide NR⁴R⁵ (right)

| Ex. No. | NR⁴R⁵ | m.p.[° C.] |
|---|---|---|
| 33 | NH-(2,2-dimethyl-tetrahydrothiophene-1,1-dioxide-4-yl) | |
| 34 | NH-(2-methyl-tetrahydrothiophene-1-oxide-4-yl) | |
| 35 | NH-(2-methyl-tetrahydrothiophene-1,1-dioxide-4-yl) | 150-152 |
| 36 | NH-(2,2-dimethyl-tetrahydrothiophene-1-oxide-3-yl) | |
| 37 | NH-(2,2-dimethyl-tetrahydrothiophene-1,1-dioxide-3-yl) | |
| 38 | NH-(2-methyl-tetrahydrothiophene-1-oxide-3-yl) | isomer mixture, oil |
| 39 | NH-(2-methyl-tetrahydrothiophene-1,1-dioxide-3-yl) | isomer mixture, oil |
| 40 | NH-(1-methyl-pyrrolidin-3-yl) | |
| 41 | NH-(1-formyl-pyrrolidin-3-yl) | |
| 42 | NH-(1-acetyl-pyrrolidin-3-yl) | |
| 43 | NH-(1-methoxycarbonyl-pyrrolidin-3-yl) | |

| Ex. No. | NR⁴R⁵ | m.p.[° C.] |
|---|---|---|
| 44 | NH-(1-CON(CH₃)₂-pyrrolidin-3-yl) | |
| 45 | NH-(1-COC₂H₅-pyrrolidin-3-yl) | |
| 46 | NH-(1-COC₃H₇-pyrrolidin-3-yl) | |
| 47 | NH-(1-CO-i-C₃H₇-pyrrolidin-3-yl) | |
| 48 | NH-(1-COC₄H₉-pyrrolidin-3-yl) | |
| 49 | NH-(1-CO-tert.-C₄H₉-pyrrolidin-3-yl) | |
| 50 | NH-(1-benzoyl-pyrrolidin-3-yl) | |
| 51 | NH-(1-(4-methylbenzoyl)-pyrrolidin-3-yl) | |
| 52 | NH-(1-(4-chlorobenzoyl)-pyrrolidin-3-yl) | |
| 53 | NH-(1-(4-trifluoromethylbenzoyl)-pyrrolidin-3-yl) | |
| 54 | NH-(1-(4-methoxybenzoyl)-pyrrolidin-3-yl) | |

TABLE 1-continued
| Ex. No. | NR⁴R⁵ | m.p.[° C.] |
|---|---|---|
| 55 | 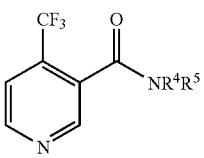 | |
| 56 | 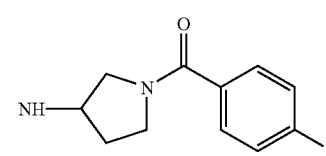 | |
| 57 | 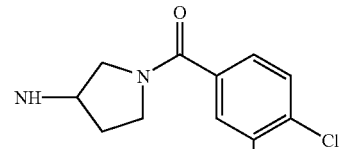 | |
| 58 | 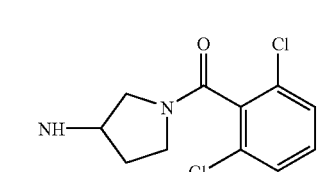 | |
| 59 | 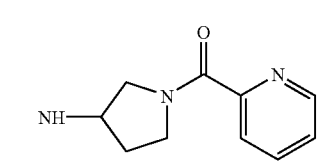 | |
| 60 | 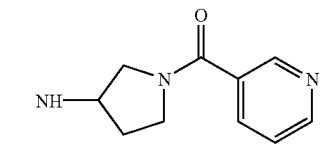 | |
| 61 | 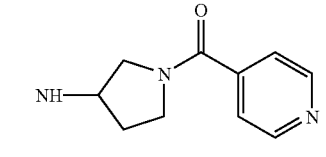 | |
| 62 | 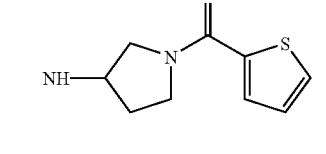 | |
| 63 | 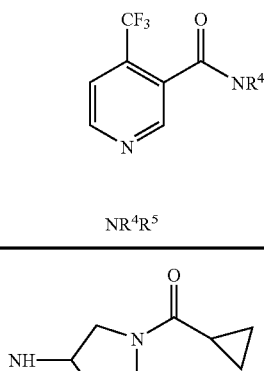 | |
| 64 | 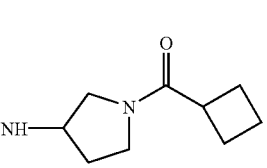 | |
| 65 | 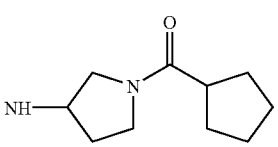 | |
| 66 | 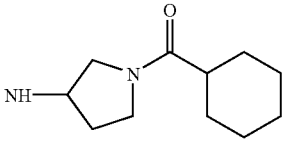 | |
| 67 | 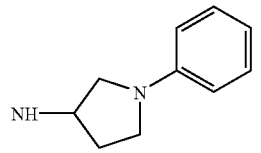 | |
| 68 | 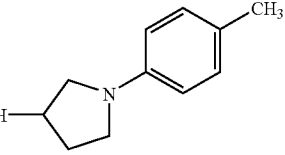 | |
| 69 | 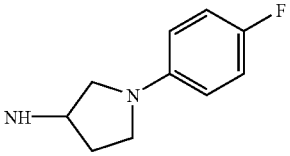 | |
| 70 | 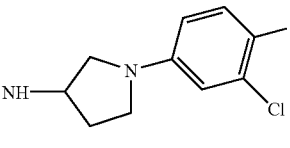 | |

TABLE 1-continued
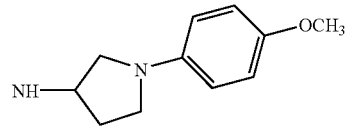
| Ex. No. | NR⁴R⁵ | m.p.[° C.] |
|---|---|---|
| 71 | 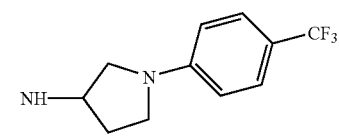 | |
| 72 | 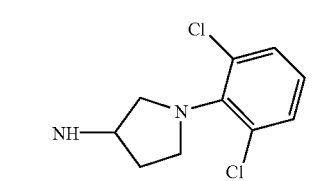 | |
| 73 | 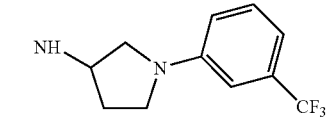 | |
| 74 | 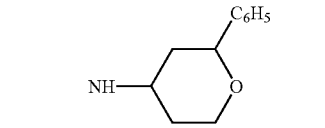 | |
| 75 | 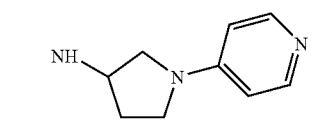 | |
| 76 | 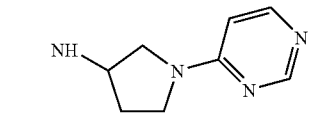 | |
| 77 | 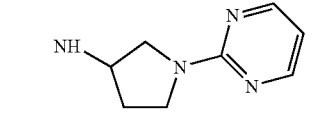 | |
| 78 | 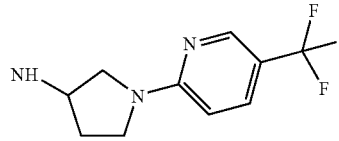 | |
| 79 | 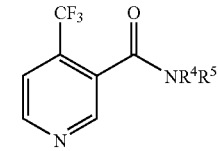 | |
TABLE 1-continued
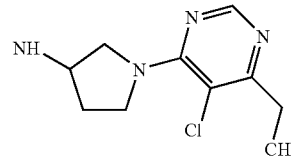
| Ex. No. | NR⁴R⁵ | m.p.[° C.] |
|---|---|---|
| 80 | 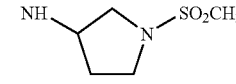 | |
| 81 | 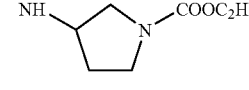 | |
| 82 | 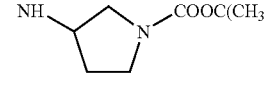 | |
| 83 | 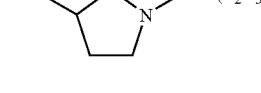 | |
| 84 | 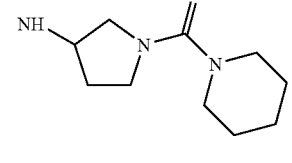 | |
| 85 | 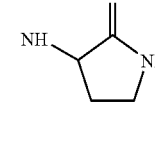 | |
| 86 | 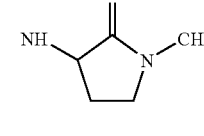 | |
| 87 | 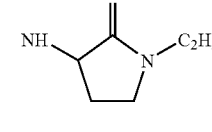 | |
| 88 | 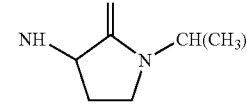 | |
| 89 | | |

TABLE 1-continued
| Ex. No. | NR⁴R⁵ | m.p.[° C.] |
|---|---|---|
| 90 | 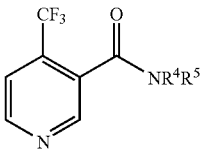 | |
| 91 | 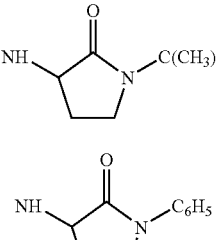 | 170-171 |
| 92 | 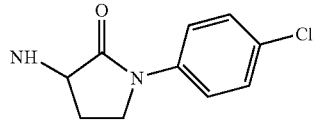 | |
| 93 | 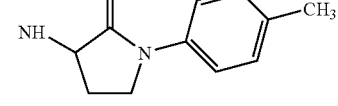 | |
| 94 | 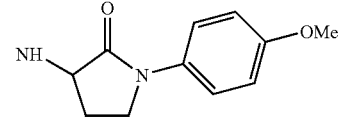 | |
| 95 | 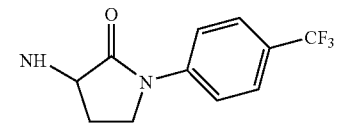 | |
| 96 | 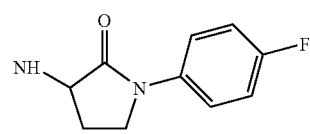 | |
| 97 | 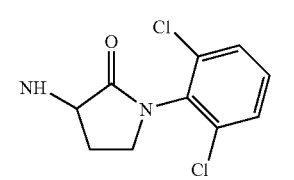 | |
| 98 | 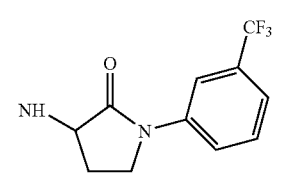 | 197—197 |
| 99 | 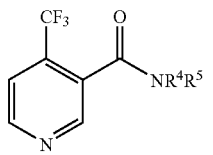 | 130-132 |
| 100 | | 195-198 |
| 101 | | 180-181 |
| 102 | 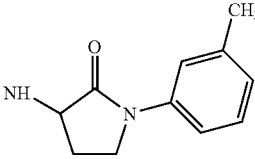 | 161-163 |
| 103 | 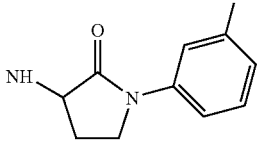 | 168-171 |
| 104 | | 164-167 |
| 105 | 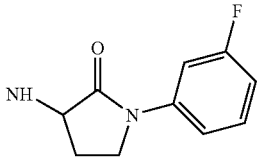 | |
| 107 | 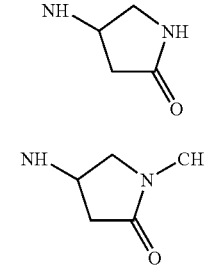 | |

TABLE 1-continued

| Ex. No. | NR⁴R⁵ | m.p.[° C.] |
|---|---|---|
| 108 | NH—[4-(1-ethyl-2-oxopyrrolidin-4-yl)] | |
| 109 | NH—[4-(1-propyl-2-oxopyrrolidin-4-yl)] | |
| 110 | NH—[4-(1-isopropyl-2-oxopyrrolidin-4-yl)] | |
| 111 | NH—[4-(1-tert-butyl-2-oxopyrrolidin-4-yl)] | |
| 112 | NH—[4-(1-phenyl-2-oxopyrrolidin-4-yl)] | |
| 113 | NH—[3-(1-methyl-2,5-dioxopyrrolidin-3-yl)] | |
| 114 | NH—[3-(1-ethyl-2,5-dioxopyrrolidin-3-yl)] | |
| 115 | NH—[3-(1-propyl-2,5-dioxopyrrolidin-3-yl)] | |
| 116 | NH—[3-(1-isopropyl-2,5-dioxopyrrolidin-3-yl)] | |
| 117 | NH—[3-(1-tert-butyl-2,5-dioxopyrrolidin-3-yl)] | |
| 118 | NH—[3-(1-phenyl-2,5-dioxopyrrolidin-3-yl)] | |
| 119 | HN(CH₃)—[3-(1-methylpyrrolidin-3-yl)] | oil |
| 120 | NH—[4-(5-phenyltetrahydrothiophen-3-yl)] | |
| 121 | NH—[3-(2-phenyltetrahydrothiophen-2-yl)] | |
| 122 | NH—[3-(2-phenyltetrahydrofuran-2-yl)] | |
| 123 | NH—[4-(5-phenyltetrahydrofuran-3-yl)] | |
| 124 | NH—(tetrahydropyran-4-yl) | 149-150 |
| 125 | NH—(2-methyltetrahydropyran-4-yl) | |

TABLE 1-continued

Structure: 4-(trifluoromethyl)pyridine-3-carboxamide (C(=O)NR⁴R⁵)

| Ex. No. | NR⁴R⁵ | m.p.[° C.] |
|---|---|---|
| 126 | 2,6-dimethyl-tetrahydropyran-4-yl-NH | |
| 127 | 3-methyl-tetrahydropyran-4-yl-NH | |
| 128 | 2,2-dimethyl-tetrahydropyran-4-yl-NH | 138 |
| 129 | 3,3-dimethyl-tetrahydropyran-4-yl-NH | |
| 130 | 2-phenyl-tetrahydropyran-4-yl-NH | |
| 131 | chroman-4-yl-NH | 197-199 |
| 132 | 8-methyl-chroman-4-yl-NH | 216-217 |
| 133 | 6,8-dimethyl-chroman-4-yl-NH | |
| 134 | 6-fluoro-8-methyl-chroman-4-yl-NH | 217-219 |
| 135 | 6-fluoro-chroman-4-yl-NH | 200-202 |
| 136 | 2-oxo-tetrahydropyran-4-yl-NH | |
| 137 | 3-methyl-2-oxo-tetrahydropyran-4-yl-NH | |
| 138 | 3,3-dimethyl-2-oxo-tetrahydropyran-4-yl-NH | |
| 139 | 6-methyl-2-oxo-tetrahydropyran-4-yl-NH | |
| 140 | 6,6-dimethyl-2-oxo-tetrahydropyran-4-yl-NH | |

TABLE 1-continued
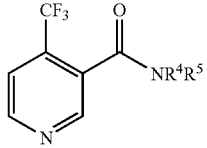
| Ex. No. | NR⁴R⁵ | m.p.[° C.] |
|---|---|---|
| 141 | 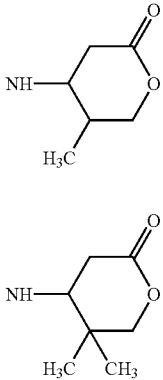 | |
| 142 | 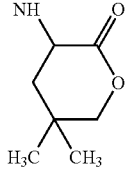 | |
| 143 | 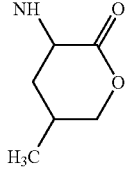 | |
| 144 | 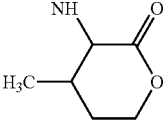 | |
| 145 | 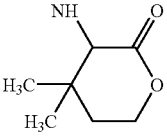 | |
| 146 | 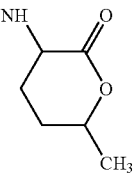 | |
| 147 | 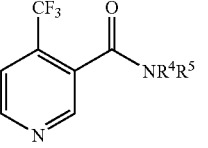 | |
TABLE 1-continued
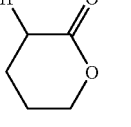
| Ex. No. | NR⁴R⁵ | m.p.[° C.] |
|---|---|---|
| 148 | 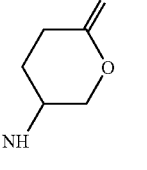 | |
| 149 | 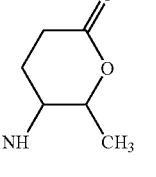 | |
| 150 | 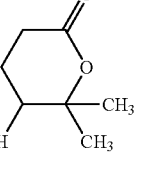 | |
| 151 | 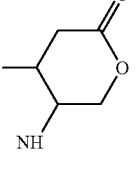 | |
| 152 | 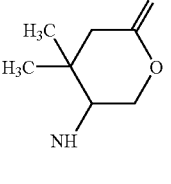 | |
| 153 | | |
| 154 | | |

TABLE 1-continued
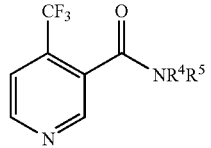
| Ex. No. | NR⁴R⁵ | m.p.[° C.] |
|---|---|---|
| 155 | 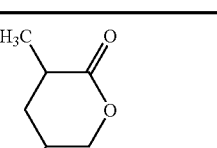 | |
| 156 | 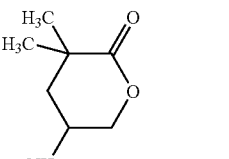 | |
| 157 | 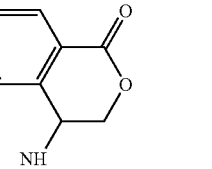 | |
| 158 | 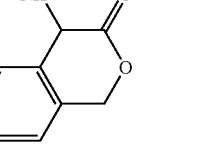 | |
| 159 | 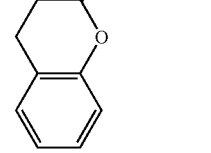 | |
| 160 | 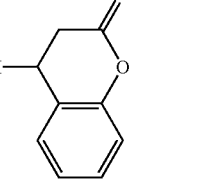 | |
| 161 | 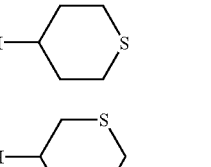 | 161-162 |
| 162 | 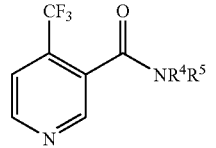 | 168-170 |
| 163 | 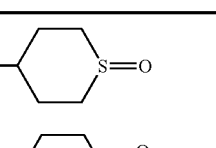 | 243 |
| 164 | 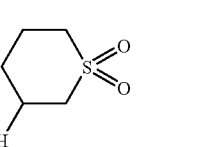 | 248 |
| 165 | 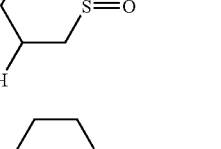 | 208-209 |
| 166 | 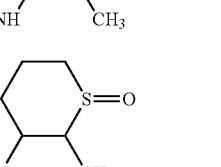 | oil |
| 167 | 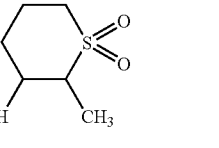 | |
| 168 | | |
| 169 | 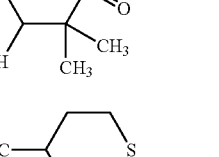 | |
| 170 | | |
| 171 | 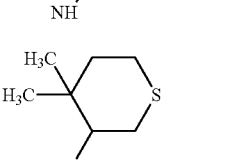 | |
| 172 | | |

TABLE 1-continued
| Ex. No. | NR⁴R⁵ | m.p.[° C.] |
|---|---|---|
| 173 | 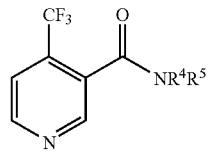 | |
| 174 | 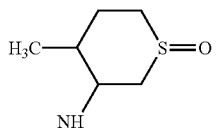 | |
| 175 | 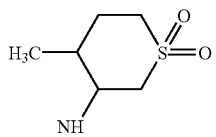 | |
| 176 | 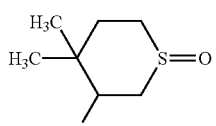 | |
| 177 | 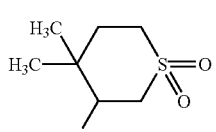 | |
| 178 | 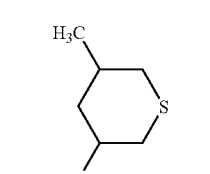 | |
| 179 | 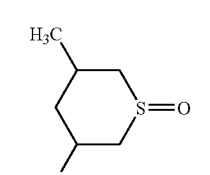 | |
| 180 | 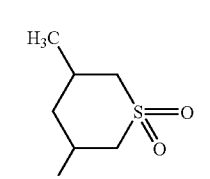 | |
TABLE 1-continued
| Ex. No. | NR⁴R⁵ | m.p.[° C.] |
|---|---|---|
| 181 | 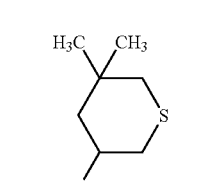 | |
| 182 | 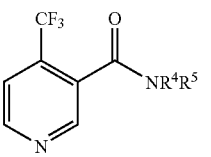 | |
| 183 | 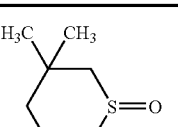 | |
| 184 | 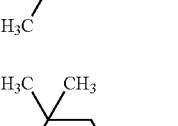 | |
| 185 | 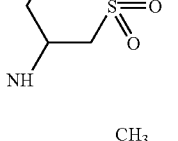 | |
| 186 | 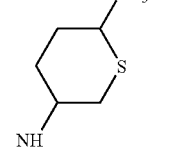 | |
| 187 | 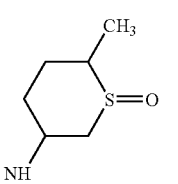 | |

TABLE 1-continued

[Structure: 4-(trifluoromethyl)pyridine-3-carboxamide with NR⁴R⁵ substituent]

| Ex. No. | NR⁴R⁵ | m.p.[° C.] |
|---|---|---|
| 188 | 3-amino-6,6-dimethyl-tetrahydrothiopyran-1,1-dioxide (NH at 3-position, two CH₃ groups geminal to SO₂) | |
| 189 | 3-amino-2,2-dimethyl-tetrahydrothiopyran | |
| 190 | 3-amino-2,2-dimethyl-tetrahydrothiopyran-1-oxide | |
| 191 | 4-amino-2-methyl-tetrahydrothiopyran | |
| 192 | 4-amino-2-methyl-tetrahydrothiopyran-1-oxide | |
| 193 | 4-amino-2-methyl-tetrahydrothiopyran-1,1-dioxide | |
| 194 | 4-amino-2,2-dimethyl-tetrahydrothiopyran | |
| 195 | 4-amino-2,2-dimethyl-tetrahydrothiopyran-1-oxide | |
| 196 | 4-amino-2,2-dimethyl-tetrahydrothiopyran-1,1-dioxide | |
| 197 | 4-amino-3-methyl-tetrahydrothiopyran | |
| 198 | 4-amino-3-methyl-tetrahydrothiopyran-1-oxide | |
| 199 | 4-amino-3-methyl-tetrahydrothiopyran-1,1-dioxide | |
| 200 | 4-amino-3,3-dimethyl-tetrahydrothiopyran | |
| 201 | 4-amino-3,3-dimethyl-tetrahydrothiopyran-1-oxide | |
| 202 | 4-amino-3,3-dimethyl-tetrahydrothiopyran-1,1-dioxide | |
| 203 | 4-amino-2-phenyl-tetrahydrothiopyran | |
| 204 | 4-amino-thiochroman | |
| 205 | 4-amino-thiochroman-1-oxide | |

TABLE 1-continued

[Structure: 4-(trifluoromethyl)pyridine-3-carboxamide with NR⁴R⁵]

| Ex. No. | NR⁴R⁵ | m.p.[° C.] |
|---|---|---|
| 206 | 4-amino-thiochroman-1,1-dioxide (NH, benzofused, S(=O)₂) | |
| 207 | 3-amino-thiochroman (NH, benzofused, S) | |
| 208 | 3-amino-thiochroman-1-oxide (NH, benzofused, S=O) | |
| 209 | 3-amino-thiochroman-1,1-dioxide (NH, benzofused, S(=O)₂) | |
| 210 | 4-amino-isothiochroman (NH, benzofused, S) | |
| 211 | 4-amino-isothiochroman-2-oxide (NH, benzofused, S=O) | |
| 212 | 4-amino-isothiochroman-2,2-dioxide (NH, benzofused, S(=O)₂) | |
| 213 | NH—(1-methylpiperidin-4-yl) | |
| 214 | NH—(1-formylpiperidin-4-yl) (N—CHO) | |
| 215 | NH—(1-acetylpiperidin-4-yl) (N—COCH₃) | 207-209 |
| 216 | NH—(1-(ethoxycarbonyl)piperidin-4-yl) (N—COOC₂H₅) | 145-146 |
| 217 | NH—(1-(methoxycarbonyl)piperidin-4-yl) (N—COOCH₃) | |
| 218 | NH—(1-(propoxycarbonyl)piperidin-4-yl) (N—COOC₃H₇) | |
| 219 | NH—(1-(isopropoxycarbonyl)piperidin-4-yl) (N—COOCH(CH₃)₂) | |
| 220 | NH—(1-(tert-butoxycarbonyl)piperidin-4-yl) (N—COOC(CH₃)₃) | 93-96 |
| 221 | NH—(1-propionylpiperidin-4-yl) (N—COC₂H₅) | |
| 222 | NH—(1-butyrylpiperidin-4-yl) (N—COC₃H₇) | |
| 223 | NH—(1-isobutyrylpiperidin-4-yl) (N—COCH(CH₃)₂) | |

TABLE 1-continued

[Structure: 4-CF3-pyridine-3-C(O)-NR⁴R⁵]

| Ex. No. | NR⁴R⁵ | m.p.[° C.] |
|---|---|---|
| 224 | NH-piperidine-N-COC₆H₅ | |
| 225 | NH-piperidine-N-CON(CH₃)₂ | |
| 226 | NH-piperidine-N-CON(C₂H₅)₂ | |
| 227 | NH-piperidine-N-CO-N-piperidine | |
| 228 | NH-piperidine-N-SO₂CH₃ | |
| 229 | NH-piperidine-N-C₆H₅ | |
| 230 | NH-piperidine-N-C₆H₄-Cl | |
| 231 | NH-piperidine-N-C₆H₄-F | 193 |
| 232 | NH-piperidine-N-C₆H₄-CH₃ | |
| 233 | NH-piperidine-N-C₆H₄-CH(CH₃)₂ | 152-153 |
| 234 | NH-piperidine-N-C₆H₄-OMe | 178 |
| 235 | NH-piperidine-N-pyrimidin-2-yl | |
| 236 | NH-(3-piperidinyl)-N-CH₃ | |

TABLE 1-continued

[Structure: 4-CF3-pyridine-3-C(O)-NR⁴R⁵]

| Ex. No. | NR⁴R⁵ | m.p.[° C.] |
|---|---|---|
| 237 | NH-(3-piperidinyl)-N-CHO | |
| 238 | NH-(3-piperidinyl)-N-COCH₃ | 172-174 |
| 239 | NH-(3-piperidinyl)-N-COC₂H₅ | |
| 240 | NH-(3-piperidinyl)-N-COC₃H₇ | |
| 241 | NH-(3-piperidinyl)-N-COCH(CH₃)₂ | |
| 242 | NH-(3-piperidinyl)-N-COC(CH₃)₃ | |
| 243 | NH-(3-piperidinyl)-N-CO-cyclopropyl | |
| 244 | NH-(3-piperidinyl)-N-COC₆H₅ | |
| 245 | NH-(3-piperidinyl)-N-COOCH₃ | |
| 246 | NH-piperidine-N-COOCH₃ | |

TABLE 1-continued

Structure: 4-(trifluoromethyl)pyridine-3-carboxamide with NR⁴R⁵

| Ex. No. | NR⁴R⁵ | m.p. [° C.] |
|---|---|---|
| 247 | 4-NH-piperidine-1-CO-cyclopropyl | |
| 248 | 3-NH-piperidine-1-COOC₂H₅ | |
| 249 | 3-NH-piperidine-1-COOC₃H₇ | |
| 250 | 3-NH-piperidine-1-COOCH(CH₃)₂ | |
| 251 | 3-NH-piperidine-1-COOC(CH₃)₃ | 153–156 |
| 252 | 3-NH-piperidine-1-COC₆H₅ | |
| 253 | 3-NH-piperidine-1-CON(CH₃)₂ | |
| 254 | 3-NH-piperidine-1-CON(C₂H₅)₂ | |
| 255 | 3-NH-piperidine-1-CO-piperidine | |
| 256 | 3-NH-piperidine-1-SO₂CH₃ | |
| 257 | 5-NH-2-oxopiperidine (NH) | |
| 258 | 5-NH-1-CH₃-2-oxopiperidine | |
| 259 | 5-NH-1-C₂H₅-2-oxopiperidine | |
| 260 | 5-NH-1-C₃H₇-2-oxopiperidine | |
| 261 | 5-NH-1-CH(CH₃)₂-2-oxopiperidine | |
| 262 | 3-NH-2,6-dioxopiperidine (NH) | |
| 263 | 3-NH-1-CH₃-2,6-dioxopiperidine | |
| 264 | 3-NH-1-C₂H₅-2,6-dioxopiperidine | |

TABLE 1-continued
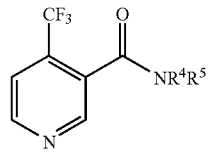
| Ex. No. | NR⁴R⁵ | m.p.[° C.] |
|---|---|---|
| 265 | 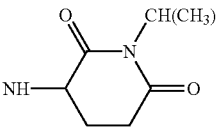 | |
| 266 | 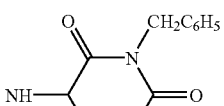 | |
| 267 | 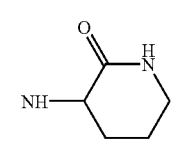 | |
| 268 | 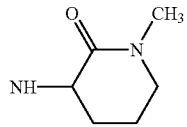 | |
| 269 | 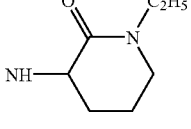 | |
| 270 | 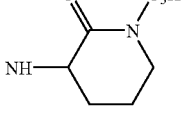 | |
| 271 | 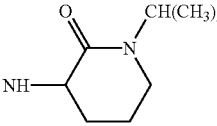 | |
| 272 | 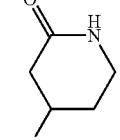 | |
| 273 | 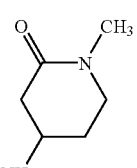 | |
TABLE 1-continued
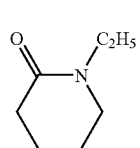
| Ex. No. | NR⁴R⁵ | m.p.[° C.] |
|---|---|---|
| 274 | 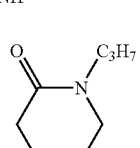 | |
| 275 | 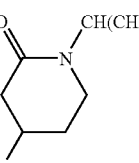 | |
| 276 | 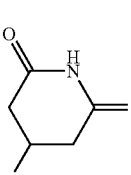 | |
| 277 | 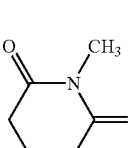 | |
| 278 | 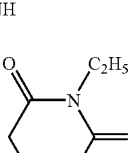 | |
| 279 | | |
| 280 | | |

TABLE 1-continued

[Structure: 4-(trifluoromethyl)pyridine-3-carboxamide with NR⁴R⁵]

| Ex. No. | NR⁴R⁵ | m.p.[° C.] |
|---|---|---|
| 281 | 1-propyl-2,6-dioxopiperidin-4-ylamino | |
| 282 | 1-isopropyl-2,6-dioxopiperidin-4-ylamino | |
| 283 | 1-phenyl-2,6-dioxopiperidin-4-ylamino | |
| 284 | 1-benzyl-2,6-dioxopiperidin-4-ylamino | |
| 285 | 1-methyl-1,2,3,4-tetrahydroquinolin-4-ylamino | |
| 286 | 1-acetyl-1,2,3,4-tetrahydroquinolin-4-ylamino | |
| 287 | oxepan-3-ylamino | |
| 288 | thiepan-3-ylamino | |
| 289 | 1-oxo-thiepan-3-ylamino | |
| 290 | 1,1-dioxo-thiepan-3-ylamino | |
| 291 | oxepan-4-ylamino | |
| 292 | thiepan-4-ylamino | |
| 293 | 1-oxo-thiepan-4-ylamino | |
| 294 | 1,1-dioxo-thiepan-4-ylamino | |
| 295 | 1-methyl-azepan-3-ylamino | |
| 296 | 1-phenyl-azepan-3-ylamino | |
| 297 | 1-acetyl-azepan-3-ylamino | |

TABLE 1-continued
| Ex. No. | NR⁴R⁵ | m.p.[° C.] |
|---|---|---|
| 298 | 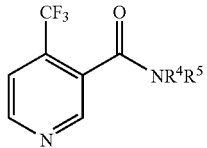 | |
| 299 | 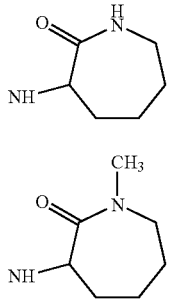 | |
| 300 | 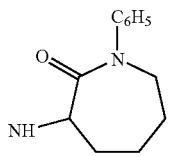 | |
| 301 | 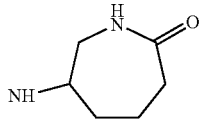 | |
| 302 | 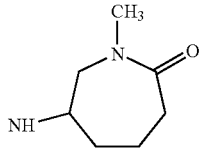 | |
| 303 | 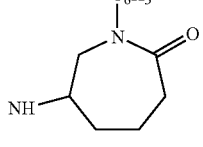 | |
| 304 | 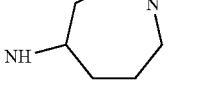 | |
| 305 |  | |
| 306 | 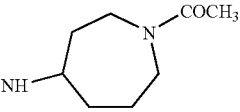 | |
| 307 | 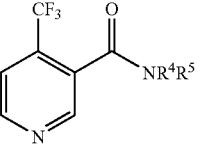 | |
| 308 | 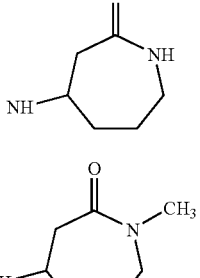 | |
| 309 | 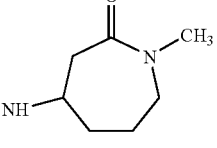 | |
| 310 | 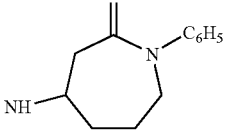 | |
| 311 | 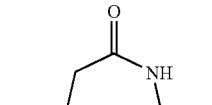 | |
| 312 | 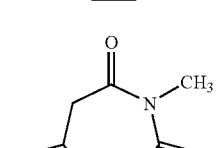 | |
| 313 | 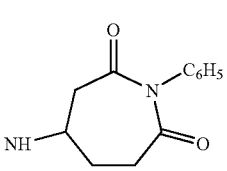 | |
| 314 | 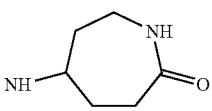 | |
| 315 | 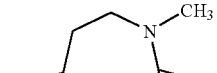 | |

TABLE 1-continued
[Structure: 4-(trifluoromethyl)pyridine-3-carboxamide with NR⁴R⁵]
| Ex. No. | NR⁴R⁵ | m.p.[° C.] |
|---|---|---|
| 316 | 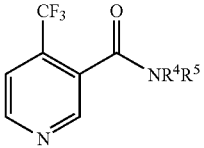 | |
| 317 | 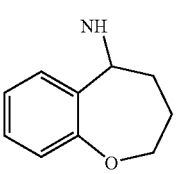 | |
| 318 | 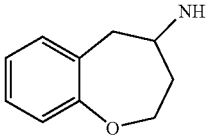 | |
| 319 | 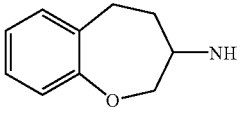 | |
| 320 | 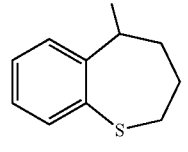 | |
| 321 | 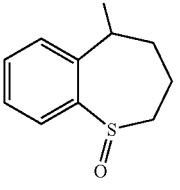 | |
| 322 | 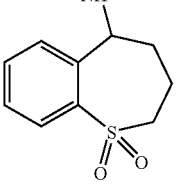 | |
| 323 | 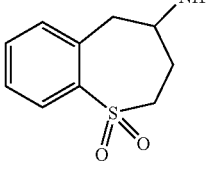 | |
| 324 | 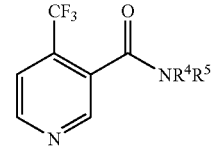 | |
| 325 | 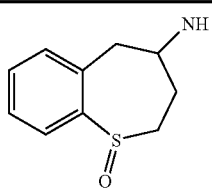 | |
| 326 | 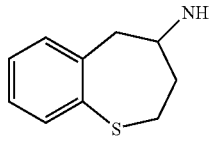 | |
| 327 | 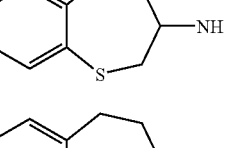 | |
| 328 | 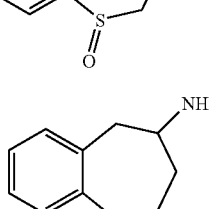 | 191–192 |
| 329 | 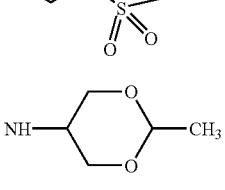 | |
| 330 | 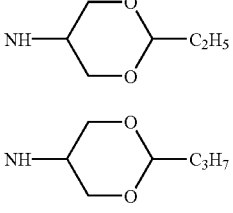 | |
| 331 | 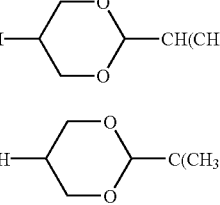 | oil |
| 332 | 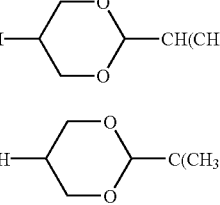 | |

TABLE 1-continued
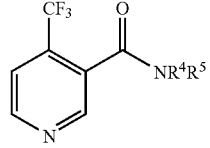
| Ex. No. | NR⁴R⁵ | m.p.[° C.] |
|---|---|---|
| 333 | 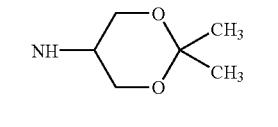 | 155-156 |
| 334 | 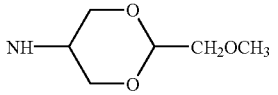 | 133-134 |
| 335 | 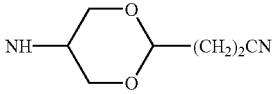 | oil |
| 336 | 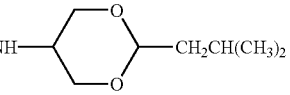 | oil |
| 337 | 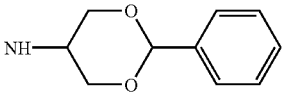 | 95-96 |
| 338 | 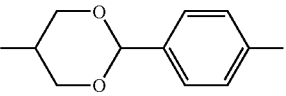 | 164-165 |
| 339 | 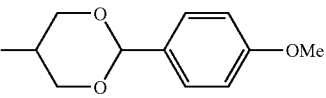 | |
| 340 | 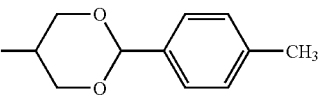 | |
| 341 | 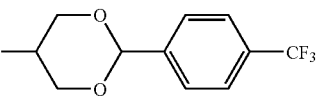 | |
| 342 | 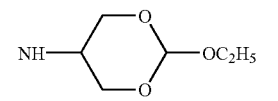 | |
| 343 | 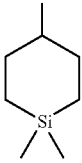 | 104 |
TABLE 1-continued
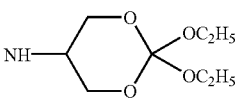
| Ex. No. | NR⁴R⁵ | m.p.[° C.] |
|---|---|---|
| 344 | 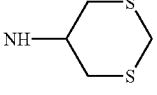 | oil |
| 345 | 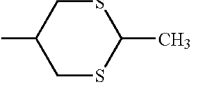 | 122-123 |
| 346 | 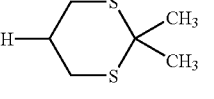 | |
| 347 | 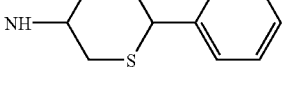 | |
| 348 | 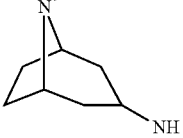 | |
| 349 | 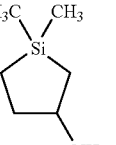 | |
| 350 | 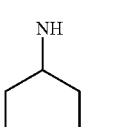 | |
| 351 | | |
| 352 | | |

TABLE 1-continued
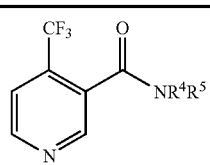
| Ex. No. | NR⁴R⁵ | m.p.[° C.] |
|---|---|---|
| 353 | 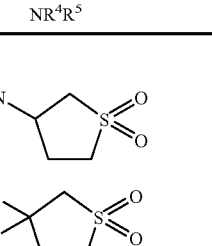 | 38-41 |
| 354 | 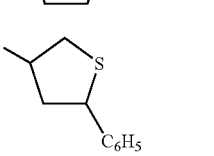 | 149-152 |
| 355 | 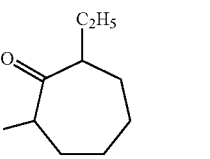 | 152-154 |
| 356 | 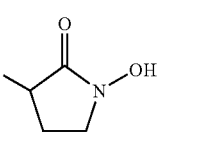 | 38-41 |
| 357 | 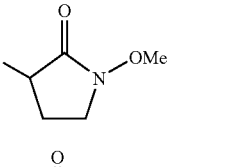 | |
| 358 | 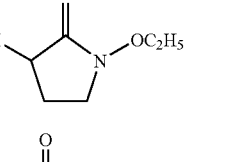 | |
| 359 | 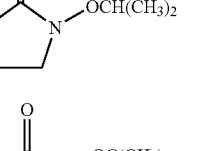 | |
| 360 | 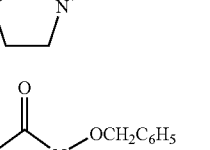 | |
| 361 |  | |
| 362 | 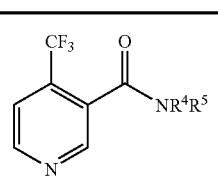 | |
TABLE 1-continued
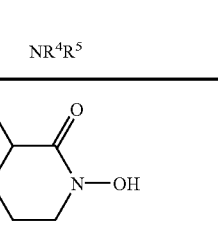
| Ex. No. | NR⁴R⁵ | m.p.[° C.] |
|---|---|---|
| 363 | 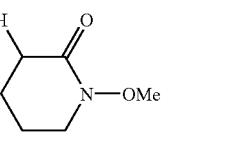 | |
| 364 | 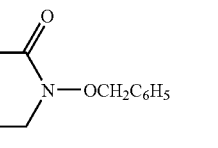 | |
| 365 | 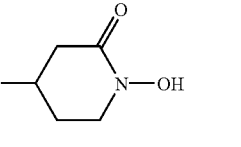 | |
| 366 | 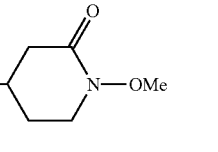 | |
| 367 | 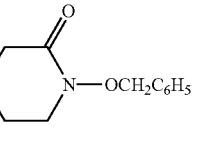 | |
| 368 | 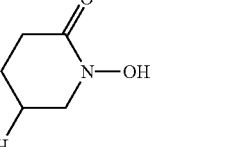 | |
| 369 | 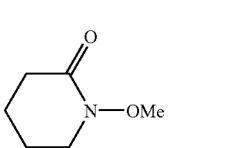 | |
| 370 |  | |

TABLE 1-continued

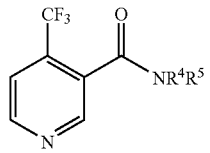

| Ex. No. | NR⁴R⁵ | m.p.[° C.] |
|---|---|---|
| 371 | (piperidinone with N—OCH₂C₆H₅ and NH substituent) | |

TABLE 2

(pyrimidine core: 4-CF₃, 5-C(=O)NR⁴R⁵)

| Ex. No. | NR⁴R⁵ | m.p. [° C.] |
|---|---|---|
| 372 | NH-(tetrahydrofuran-3-yl) | |
| 373 | NH-(3-yl of γ-butyrolactone) | |
| 374 | NH-(3-yl of 5,5-dimethyl-γ-butyrolactone) | |
| 375 | NH-(3-yl of 4,4-dimethyl-γ-butyrolactone) | |
| 376 | NH-(tetrahydropyran-4-yl) | |
| 377 | NH-(tetrahydropyran-3-yl) | |
| 378 | NH-(tetrahydrothiophen-3-yl) | |
| 379 | NH-(tetrahydrothiophen-3-yl S-oxide) | |
| 380 | NH-(tetrahydrothiophen-3-yl S,S-dioxide) | |
| 381 | NH-(tetrahydrothiopyran-4-yl) | |
| 382 | NH-(tetrahydrothiopyran-4-yl S-oxide) | |
| 383 | NH-(tetrahydrothiopyran-4-yl S,S-dioxide) | |
| 384 | NH-(tetrahydrothiopyran-3-yl) | |
| 385 | NH-(tetrahydrothiopyran-3-yl S-oxide) | |
| 386 | NH-(tetrahydrothiopyran-3-yl S,S-dioxide) | |
| 387 | NH-(1-benzoylpiperidin-4-yl), N—COC₆H₅ | |
| 388 | NH-(1-Boc-piperidin-4-yl), N—COOC(CH₃)₃ | |

B. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexane as solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and these are dried and mixed intimately. The wettable powder amounts to approx. 5% by weight and the inert carrier material to approx. 95% by weight of the finished granules.

C. BIOLOGICAL EXAMPLES

In Examples 1 to 3 below, compounds are considered to be active when, at a concentration of 500 ppm (based on the content of active compound) or less, they have an effect on the harmful organisms of 50% or more.

Example 1

Germinated field bean seeds (Vicia faba) with seed roots were transferred into brown glass bottles filled with tap water and then populated with about 100 black bean aphids (Aphis fabae). Plants and aphids were then dipped into an aqueous solution of the formulated compound to be examined for 5 seconds. After they had drained, plants and animals were stored in a climatized chamber (16 hours of light/day, 25° C., 40-60% relative atmospheric humidity). After 3 and 6 days of storage, the mortality of the compound on the aphids was determined. The compounds of the following examples were active: 3, 8, 9, 11, 17, 18, 19, 21, 22 (cis), 22 (trans), 24, 30 (cis), 30 (trans), 31 (cis), 124, 134, 135, 161, 163, 164, 166, 203, 216, 219, 353 and 356.

Example 2

Germinated field bean seeds (Vicia faba) with seed roots were transferred into brown glass bottles filled with tap water. Four milliliters of an aqueous solution of the formulated compound to be examined were pipetted into the brown glass bottle. The field bean was then heavily populated with about 100 black bean aphids (Aphis fabae). Plants and aphids were then stored in a climatized chamber (16 hours of light/day, 25° C., 40-60% relative atmospheric humidity). After 3 and 6 days of storage, the root-systemic effect of the compound as aphid mortality was determined. The compounds of the following examples were active: 3, 8, 9, 10, 11, 12, 17, 18, 19, 21, 22 (cis), 22 (trans), 24, 30 (cis), 30 (trans), 31 (cis), 35, 124, 128, 134, 135, 161, 162, 163, 164, 165, 166, 203, 216, 219, 237, 250, 353 and 356.

Example 3

Bush beans (Phaseolus vulgaris) having in each case two well-developed leaves were sprayed to runoff point with an aqueous solution of the formulated compound to be examined. After drying, in each case one treated bean plant, one untreated bean plant and one bean plant heavily infected by white flies (Trialeurodes vaporariorum) were grouped together. The plants were placed in a greenhouse at 25° C. and 60% relative humidity. After 48 hours, the number of eggs which had been laid on the treated and the untreated bean plants was determined. The degree of repellent action was obtained by relative comparison of the number of eggs on the untreated plant (corresponds in each case to 100%) with the number of eggs on the treated plant. In this repellent test, the compound of the following example was active: 19.

Example 4

Soybeabean plants with three well grown leaves were sprayed to runoff point with an aqueous solution of the formulated compound After drying, in each case one treated plant and one untreated plant were put together with a plant which was infested with a population of the thrips species Frankliniella occidentalis. The plants were stored in a climatic chamber (23° C., 50-60% relative atmospheric humidity). 14 days after treatment the leaf damage was determined on the treated and the untreated plant. The degree of repellent action was obtained by relative comparison of the leaf damage of the untreated plant (corresponds in each case to 100%) with the leaf damage of the treated plant. In this repellent test, the compound of the following example was active: 19.

What is claimed is:

1. An amide of the formula (I) or a salt thereof

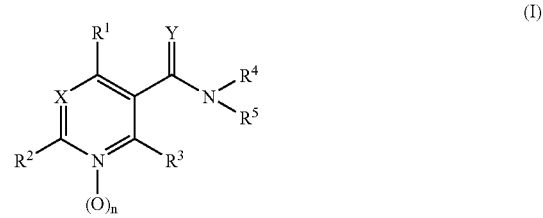

(I)

where the symbols and indices are as defined below:

X is CH;
Y is O or S;
n is 0 or 1;
$R^1$ is $(C_1\text{-}C_4)$-haloalkyl;
$R^2$, $R^3$ are hydrogen
$R^4$ is hydrogen, $(C_1\text{-}C_{10})$-alkyl, $(C_3\text{-}C_{10})$-cycloalkyl, $(C_3\text{-}C_{10})$-alkenyl or $(C_3\text{-}C_{10})$-alkynyl, where the alkyl, cycloalkyl, alkenyl or alkynyl groups are unsubstituted or substituted by up to three halogen atoms, in the case of fluorine also up to the maximum number;
$R^5$ is a non-aromatic heterocycle which contains at least one oxygen, nitrogen and/or silicon ring atom, which is unsubstituted or substituted by one to six monovalent groups and which may be part of a spirocyclic, fused or bicyclic ring system.

2. An amide of the formula (I) or a salt thereof as claimed in claim 1, where $R^5$ is a four- to eight-membered non-aromatic heterocycle which contains one oxygen ring atom, one nitrogen atom, one silicon ring atom or two oxygen ring atoms.

3. An amide of the formula (I) or a salt thereof as claimed in claim 1, where $R^5$ is a non-aromatic radical of the formula (II)

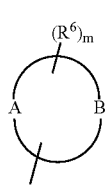

in which A and/or B is/are at least one oxygen, nitrogen or silicon ring atom and the ring may additionally contain one or two carbonyl groups which, together with the hetero units, may form a lactone, lactam or imide unit; and where, if A is oxygen and B is nitrogen, these units may be directly adjacent and where in all other cases in which A and B are heteroatom units these must be separated by at least one saturated carbon unit;

m is 0 or 1 to 6;

$R^6$ are, depending on m, identical or different and are each $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl or $(C_8-C_{10})$-cycloalkynyl which is unsubstituted or substituted by one or more identical or different radicals, or is/are a radical $R^7$, where $R^7$ is halogen, cyano, nitro, hydroxyl, amino, $(C_1-C_{10})$-alkanoyl, $(C_3-C_{10})$-alkenoyl, $(C_3-C_{10})$-alkynoyl, $(C_3-C_{10})$-cycloalkanoyl, $(C_1-C_{10})$-alkoxy, $(C_3-C_{10})$-alkenyloxy, $(C_3-C_{10})$-alkynyloxy, $(C_3-C_{10})$-cycloalkoxy, $(C_4-C_{10})$-cycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_3-C_4)$-alkenyloxy, $(C_4-C_8)$-cycloalkenyl-$(C_3-C_4)$-alkenyloxy, $(C_1-C_4)$-alkyl-$(C_3-C_8)$-cycloalkoxy, $(C_2-C_4)$-alkenyl-$(C_3-C_8)$-cycloalkoxy, $(C_2-C_4)$-alkynyl-$(C_3-C_8)$-cycloalkoxy, $(C_1-C_4)$-alkyl-$(C_4-C_8)$-cycloalkenyloxy, $(C_2-C_4)$-alkenyl-$(C_4-C_8)$-cycloalkenyloxy, $(C_1-C_4)$-alkoxy-$(C_1-C_4)$-alkoxy, $(C_1-C_4)$-alkoxy-$(C_3-C_4)$-alkenyloxy, carbamoyl, $(C_1-C_8)$-mono- or -dialkylcarbamoyl, $(C_3-C_8)$-mono- or -dicycloalkylcarbamoyl, $(C_1-C_8)$-alkoxycarbonyl, $(C_3-C_8)$-cycloalkoxycarbonyl, $(C_1-C_8)$-alkanoyloxy, $(C_3-C_8)$-cycloalkanoyloxy, $(C_1-C_8)$-alkanoylamino, $(C_3-C_8)$-alkenoylamino, $(C_3-C_8)$-cycloalkanoylamino, $(C_3-C_8)$-cycloalkyl-$(C_1-C_4)$-alkanoylamino, the N-$(C_1-C_4)$-alkylamino analogs of the four last-mentioned radicals, $(C_1-C_{10})$-alkylamino, $(C_3-C_{10})$-alkenylamino, $(C_3-C_{10})$-alkynylamino, $(C_3-C_8)$-cycloalkylamino, $(C_4-C_8)$-cycloalkenylamino, $(C_3-C_8)$-cycloalkyl-$(C_1-C_4)$-alkylamino, $(C_4-C_8)$-cycloalkenyl-$(C_1-C_4)$-alkylamino, $(C_3-C_8)$-cycloalkyl-$(C_3-C_4)$-alkenylamino, $(C_4-C_8)$-cycloalkenyl-$(C_3-C_4)$-alkenylamino, $(C_1-C_4)$-alkyl-$(C_3-C_8)$-cycloalkylamino, $(C_2-C_4)$-alkenyl-$(C_3-C_8)$-cycloalkylamino, $(C_2-C_4)$-alkynyl-$(C_3-C_8)$-cycloalkylamino, $(C_1-C_4)$-alkyl-$(C_4-C_8)$-cycloalkenylamino, $(C_2-C_4)$-alkenyl-$(C_4-C_8)$-cycloalkenylamino, the N-$(C_1-C_4)$-alkylamino analogs of the fourteen last-mentioned radicals, $(C_1-C_{10})$-trialkylsilyl, aryl, aroyl, heterocyclylcarbonyl, aryloxy, arylamino, N-$(C_1-C_4)$-alkyl-arylamino, the N-$(C_1-C_4)$-alkylamino analogs of the two last-mentioned radicals, aryl-$(C_1-C_4)$-alkoxy, aryl-$(C_3-C_4)$-alkenyloxy, aryl-$(C_1-C_4)$-alkylamino, aryl-$(C_3-C_4)$-alkenylamino, the N-$(C_1-C_4)$-alkylamino analog of the last-mentioned radical, aryl-$(C_1-C_8)$-dialkylsilyl, diaryl-$(C_1-C_8)$-alkylsilyl, triarylsilyl, heterocyclyl, heterocyclyloxy or heterocyclylamino, where the cyclic moiety of the aryl or heterocyclyl radicals mentioned is unsubstituted or substituted by one or more radicals selected from the group consisting of halogen, cyano, nitro, amino, hydroxyl, $(C_1-C_4)$-alkyl, $(C_1-C_4)$-haloalkyl, $(C_3-C_8)$-cycloalkyl, $(C_1-C_4)$-alkoxy, $(C_1-C_4)$-haloalkoxy, $(C_1-C_4)$-alkylamino, $(C_1-C_4)$-dialkylamino, trimethylsilyl and $(C_1-C_4)$-alkanoyl;

where, if appropriate, two alkyl radicals $R^6$ attached to the same carbon atom may form, together with this carbon atom, a spirocyclic ring system, or where, if appropriate, two alkyl radicals $R^6$ attached to different carbon atoms may, together with the aliphatic heterocycle of the formula (II), form a fused or bicyclic ring system or furthermore the heteroaliphatic ring system of the formula (II) and an additional aryl or heteroaryl system together may form a fused ring system; and where, if $R^6$ is $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl oder $(C_8-C_{10})$-cycloalkynyl, the radicals mentioned may be unsubstituted or mono- or polysubstituted by radicals $R^{11}$, where $R^{11}$ has the meanings given above for $R^7$, and all groups mentioned for $R^6$, $R^7$ and $R^{11}$, are unsubstituted or substituted by up to three halogen atoms, in the case of fluorine also up to the maximum number.

4. An amide of the formula (I) or a salt thereof as claimed in claim 3, where A and/or B are at least one —O—, —$NR^8$— or —$SiR^9R^{10}$— ring atoms, where $R^8$ is hydrogen, $(C_1-C_{10})$-alkyl, $(C_3-C_{10})$-alkenyl, $(C_3-C_{10})$-alkynyl, $(C_3-C_{10})$-cycloalkyl, $(C_4-C_{10})$-cycloalkenyl, aryl, heterocyclyl, $(C_1-C_{10})$-alkanoyl, $(C_3-C_{10})$-alkenoyl, $(C_3-C_{10})$-alkynoyl, $(C_4-C_8)$-cycloalkanoyl, aroyl, heterocyclylcarbonyl, carbamoyl, $(C_1-C_6)$-mono- or -dialkylcarbamoyl, $(C_3-C_{10})$-mono- or -dicycloalkylcarbamoyl, $(C_1-C_{10})$-alkoxycarbonyl, $(C_3-C_{10})$-cycloalkoxycarbonyl, hydroxyl, $(C_1-C_{10})$-alkoxy, $(C_3-C_{10})$-alkenyloxy, $(C_3-C_{10})$-alkynyloxy, $(C_3-C_{10})$-cycloalkoxy, $(C_4-C_{10})$-cycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_3-C_4)$-alkenyloxy, $(C_4-C_8)$-cycloalkenyl-$(C_3-C_4)$-alkenyloxy, $(C_1-C_4)$-alkyl-$(C_3-C_8)$-cycloalkoxy, $(C_2-C_4)$-alkenyl-$(C_3-C_8)$-cycloalkoxy, $(C_2-C_4)$-alkynyl-$(C_3-C_8)$-cycloalkoxy, $(C_1-C_4)$-alkyl-$(C_4-C_8)$-cycloalkenyloxy, $(C_2-C_4)$-alkenyl-$(C_4-C_8)$-cycloalkenyloxy, $(C_1-C_4)$-alkoxy-$(C_1-C_4)$-alkoxy, $(C_1-C_4)$-alkoxy-$(C_3-C_4)$-alkenyloxy, aryloxy, aryl-$(C_1-C_{10})$-alkoxy, aryl-$(C_3-C_{10})$-alkenyloxy or aryl-$(C_3-C_{10})$-alkynyloxy and where the radicals mentioned above for $R^8$ may be unsubstituted or substituted by one or more radicals selected form the group consisting of cyano, nitro, amino, hydroxyl, $(C_1-C_4)$-alkyl, $(C_3-C_{10})$-cycloalkyl, $(C_1-C_4)$-alkoxy, $(C_1-C_4)$-alkylamino or $(C_1-C_4)$-alkanoyl;

$R^9$ and $R^{10}$ are $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl, $(C_8-C_{10})$-cycloalkynyl, aryl, aryl-$(C_1-C_4)$-alkyl or heterocyclyl, and where in all groups mentioned for $R^8$, $R^9$ and $R^{10}$ are unsubstituted or substituted by one to three halogen atoms, in the case of fluorine also up to the maximum number.

5. An amide of the formula (I) or a salt thereof as claimed in claim 3, where $R^5$ is a five- to seven-membered non-aromatic heterocycle of the formula (II) having one or two heteroatom units A and/or B and additionally one carbonyl group in the ring, which carbonyl group, together with the hetero unit(s), forms a lactone or lactam unit.

6. An amide of the formula (I) or a salt thereof as claimed in claim 1 where X is —CH—, Y is —O— and n is 0.

7. An amide of the formula (I) or a salt thereof as claimed in claim 1 where $R^1$ is $(C_1-C_4)$-alkyl which is mono- or polysubstituted by F and/or Cl.

8. An amide of the formula (I) or a salt thereof as claimed in claim 7 where $R^1$ is $CF_3$, $CHF_2$ or $CF_2Cl$.

9. An amide of the formula (I) or a salt thereof as claimed in claim 8 where $R^1$ is $CF_3$.

10. A composition for controlling endo- and/or ectoparasites having insecticidal, acaricidal, ixodicidal, nematicidal, molluscicidal and/or fungicidal action, which comprises at least one compound of the formula (I) or a salt thereof and a mixture with carries and/or surfactants as claimed in claim 1.

11. A method for controlling harmful insects, acarids and/or nematodes which comprises applying an effective amount of a compound of the formula (I) or a salt thereof as claimed in claim 1 to these pests, or to the plants, areas or substrates infested with them.

12. A method for fending off, or warding off, harmful organisms, where one or more compounds of the formula (I) or their salts as claimed in claim 1 are applied to the site from which the harmful organisms are to be fended off or warded off.

13. An amide of the formula (I) or a salt thereof

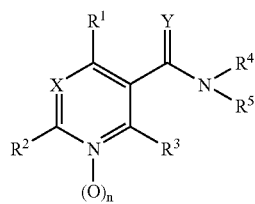

(I)

where the symbols and indices are as defined below:
X is CH;
Y is O or S;
n is 0 or 1;
$R^1$ is $(C_1-C_4)$-haloalkyl;
$R^2$, $R^3$ are hydrogen
$R^4$ is hydrogen, $(C_1-C_{10})$-alkyl, $(C_3-C_{10})$-cycloalkyl, $(C_3-C_{10})$-alkenyl or $(C_3-C_{10})$-alkynyl, where the alkyl, cycloalkyl, alkenyl or alkynyl groups are unsubstituted or substituted by up to three halogen atoms, in the case of fluorine also up to the maximum number;

where $R^5$ is a non-aromatic radical of the formula (II)

(II)

in which A and/or B is/are at least one oxygen, nitrogen or silicon ring atom and the ring may additionally contain one or two carbonyl groups which, together with the hetero units, may form a lactone, lactam or imide unit; and where, if A is oxygen and B is nitrogen, these units may be directly adjacent and where in all other cases in which A and B are heteroatom units these must be separated by at least one saturated carbon unit;

m is 0 or 1 to 6;

$R^6$ is $(C_1-C_{10})$-alkyl, $(C_2-C_{10})$-alkenyl, $(C_2-C_{10})$-alkynyl, $(C_3-C_{10})$-cycloalkyl, $(C_4-C_{10})$-cycloalkenyl or $(C_8-C_{10})$-cycloalkynyl and the radicals mentioned are unsubstituted or mono- or polysubstituted by radicals $R^{11}$, where $R^{11}$ has the meanings given above for $R^7$, and all groups mentioned for $R^6$, $R^7$ and $R^{11}$, are unsubstituted or substituted by up to three halogen atoms, in the case of fluorine also up to the maximum number $R^7$ is halogen, cyano, nitro, hydroxyl, amino, $(C_1-C_{10})$-alkanoyl, $(C_3-C_{10})$-alkenoyl, $(C_3-C_{10})$-alkynoyl, $(C_3-C_{10})$-cycloalkanoyl, $(C_1-C_{10})$-alkoxy, $(C_3-C_{10})$-alkenyloxy, $(C_3-C_{10})$-alkynyloxy, $(C_3-C_{10})$-cycloalkoxy, $(C_4-C_{10})$-cycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_3-C_4)$-alkenyloxy, $(C_4-C_8)$-cycloalkenyl-$(C_3-C_4)$-alkenyloxy, $(C_1-C_4)$-alkyl-$(C_3-C_8)$-cycloalkoxy, $(C_2-C_4)$-alkenyl-$(C_3-C_8)$-cycloalkoxy, $(C_2-C_4)$-alkynyl-$(C_3-C_8)$-cycloalkoxy, $(C_1-C_4)$-alkyl-$(C_4-C_8)$-cycloalkenyloxy, $(C_2-C_4)$-alkenyl-$(C_4-C_8)$-cycloalkenyloxy, $(C_1-C_4)$-alkoxy-$(C_1-C_4)$-alkoxy, $(C_1-C_4)$-alkoxy-$(C_3-C_4)$-alkenyloxy, carbamoyl, $(C_1-C_8)$-mono- or -dialkylcarbamoyl, $(C_3-C_8)$-mono- or -dicycloalkylcarbamoyl, $(C_1-C_8)$-alkoxycarbonyl, $(C_3-C_8)$-cycloalkoxycarbonyl, $(C_1-C_8)$-alkanoyloxy, $(C_3-C_8)$-cycloalkanoyloxy, $(C_1-C_8)$-alkanoylamino, $(C_3-C_8)$-alkenoylamino, $(C_3-C_8)$-cycloalkanoylamino, $(C_3-C_8)$-cycloalkyl-$(C_1-C_4)$-alkanoylamino, the N-$(C_1-C_4)$-alkylamino analogs of the four last-mentioned radicals, $(C_1-C_{10})$-alkylamino, $(C_3-C_{10})$-alkenylamino, $(C_3-C_{10})$-alkynylamino, $(C_3-C_8)$-cycloalkylamino, $(C_4-C_8)$-cycloalkenylamino, $(C_3-C_8)$-cycloalkyl-$(C_1-C_4)$-alkylamino, $(C_4-C_8)$-cycloalkenyl-$(C_1-C_4)$-alkylamino, $(C_3-C_8)$-cycloalkyl-$(C_3-C_4)$-alkenylamino, $(C_4-C_8)$-cycloalkenyl-$(C_3-C_4)$-alkenylamino, $(C_1-C_4)$-alkyl-$(C_3-C_8)$-cycloalkylamino, $(C_2-C_4)$-alkenyl-$(C_3-C_8)$-cycloalkylamino, $(C_2-C_4)$-alkynyl-$(C_3-C_8)$-cycloalkylamino, $(C_1-C_4)$-alkyl-$(C_4-C_8)$-cycloalkenylamino, $(C_2-C_4)$-alkenyl-$(C_4-C_8)$-cycloalkenylamino, the N-$(C_1-C_4)$-alkylamino analogs of the fourteen last-mentioned radicals, $(C_1-C_{10})$-trialkylsilyl, aryl, aroyl, heterocyclylcarbonyl, aryloxy, arylamino, N-$(C_1-C_4)$-alkyl-arylamino, the N-$(C_1-C_4)$-alkylamino analogs of the two last-mentioned radicals, aryl-$(C_1-C_4)$-alkoxy, aryl-$(C_3-C_4)$-alkenyloxy, aryl- ($C_1$-$C_4$)-alkylamino, aryl-($C_3$-$C_4$)-alkenylamino, the N-($C_1$-$C_4$)-alkylamino analog of the last-mentioned radical, aryl-($C_1$-$C_8$)-dialkylsilyl, diaryl-($C_1$-$C_8$)-alkylsilyl, triarylsilyl, heterocyclyl, heterocyclyloxy or heterocyclylamino, where the cyclic moiety of the aryl or heterocyclyl radicals mentioned is unsubstituted or substituted by one or more radicals selected from the group consisting of halogen, cyano, nitro, amino, hydroxyl, ($C_1$-$C_4$)-alkyl, ($C_1$-$C_4$)-haloalkyl, ($C_3$-$C_8$)-cycloalkyl, ($C_1$-$C_4$)-alkoxy, ($C_1$-$C_4$)-haloalkoxy, ($C_1$-$C_4$)-alkylamino, ($C_1$-$C_4$)-dialkylamino, trimethylsilyl and ($C_1$-$C_4$)-alkanoyl;

where, if appropriate, two alkyl radicals $R^6$ attached to the same carbon atom may form, together with this carbon atom, a spirocyclic ring system, or where, if appropriate, two alkyl radicals $R^6$ attached to different carbon atoms may, together with the aliphatic heterocycle of the formula (II), form a fused or bicyclic ring system or furthermore the heteroaliphatic ring system of the formula (II) and an additional aryl or heteroaryl system together may form a fused ring system;

and where, if $R^6$ is ($C_1$-$C_{10}$)-alkyl, ($C_2$-$C_{10}$)-alkenyl, ($C_2$-$C_{10}$)-alkynyl, ($C_3$-$C_{10}$)-cycloalkyl, ($C_4$-$C_{10}$)-cycloalkenyl oder ($C_8$-$C_{10}$)-cycloalkynyl, the radicals mentioned may be unsubstituted or mono- or polysubstituted by radicals $R^{11}$.

14. An amide of the formula (I) or a salt thereof

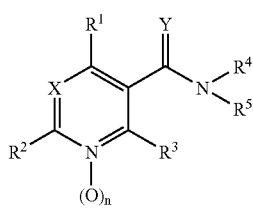

where the symbols and indices are as defined below:
X is CH;
Y is O or S;
n is 0 or 1;
$R^1$ is ($C_1$-$C_4$)-haloalkyl;
$R^2$, $R^3$ are hydrogen
$R^4$ is hydrogen, ($C_1$-$C_{10}$)-alkyl, ($C_3$-$C_{10}$)-cycloalkyl, ($C_3$-$C_{10}$)-alkenyl or ($C_3$-$C_{10}$)-alkynyl, where the alkyl, cycloalkyl, alkenyl or alkynyl groups are unsubstituted or substituted by up to three halogen atoms, in the case of fluorine also up to the maximum number,
where $R^5$ is a non-aromatic radical of the formula (II)

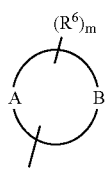

in which A and/or B is/are at least one oxygen, nitrogen or silicon ring atom and the ring may additionally contain one or two carbonyl groups which, together with the hetero units, may form a lactone, lactam or imide unit; and where, if A is oxygen and B is nitrogen, these units may be directly adjacent and where in all other cases in which A and B are heteroatom units these must be separated by at least one saturated carbon unit;

m is 0 or 1 to 6;
$R^6$ is ($C_1$-$C_{10}$)-alkyl, ($C_2$-$C_{10}$)-alkenyl, ($C_2$-$C_{10}$)-alkynyl, ($C_3$-$C_{10}$)-cycloalkyl, ($C_4$-$C_{10}$)-cycloalkenyl or ($C_8$-$C_{10}$)-cycloalkynyl and the radicals mentioned are unsubstituted or mono- or polysubstituted by radicals $R^{11}$, where $R^{11}$ has the meanings given above for $R^7$, and all groups mentioned for $R^6$, $R^7$ and $R^{11}$, are unsubstituted or substituted by up to three halogen atoms, in the case of fluorine also up to the maximum number $R^7$ is selected from the group consisting of aryl, aroyl, heterocyclylcarbonyl, aryloxy, arylamino, N-($C_1$-$C_4$)-alkyl-arylamino, the N-($C_1$-$C_4$)-alkylamino analogs of the two last-mentioned radicals, aryl-($C_1$-$C_4$)-alkoxy, aryl-($C_3$-$C_4$)-alkenyloxy, aryl-($C_1$-$C_4$)-alkylamino, aryl-($C_3$-$C_4$)-alkenylamino, the N-($C_1$-$C_4$)-alkylamino analog of the last-mentioned radical, aryl-($C_1$-$C_8$)-dialkylsilyl, diaryl-($C_1$-$C_8$)-alkylsilyl, triarylsilyl, heterocyclyl, heterocyclyloxy and heterocyclylamino, where the cyclic moiety of the aryl or heterocyclyl radicals mentioned is unsubstituted or substituted by one or more radicals selected from the group consisting of halogen, cyano, nitro, amino, hydroxyl, ($C_1$-$C_4$)-alkyl, ($C_1$-$C_4$)-haloalkyl, ($C_3$-$C_8$)-cycloalkyl, ($C_1$-$C_4$)-alkoxy, ($C_1$-$C_4$)-alkylamino and ($C_1$-$C_4$)-alkanoyl.

15. An amide of the formula (I) or a salt thereof

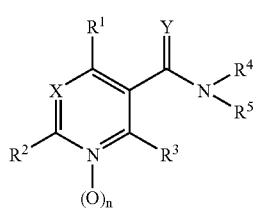

where the symbols and indices are as defined below:
X is CH;
Y is O or S;
n is 0 or 1;
$R^1$ is ($C_1$-$C_4$)-haloalkyl;
$R^2$, $R^3$ are hydrogen
$R^4$ is hydrogen
$R^5$ is a non-aromatic heterocycle which contains at least one oxygen, nitrogen and/or silicon ring atom, which is unsubstituted or substituted by one to six monovalent groups and which may be part of a spirocyclic, fused or bicyclic ring system.

16. A process for preparing an amide of the formula (I) or a salt thereof which

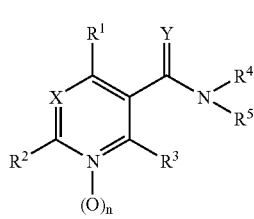

comprises reacting a carboxylic acid of formula (III)

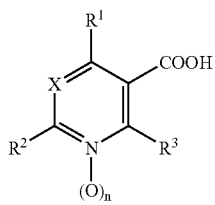

(III)

in the form of an activated derivative of this acid in the presence of a base with a compound of the formula (IV)

HNR⁴R⁵ in where the symbols and indices are defined below:
X is CH;
Y is O or S;
n is 0 or 1;
$R^1$ is $(C_1-C_4)$-haloalkyl;
$R^2$, $R^3$ are hydrogen
$R^4$ is hydrogen, $(C_1-C_{10})$-alkyl, $(C_3-C_{10})$-cycloalkyl, $(C_3-C_{10})$-alkenyl or $(C_3-C_{10})$-alkynyl, where the alkyl, cycloalkyl, alkenyl or alkynyl groups are unsubstituted or substituted by up to three halogen atoms, in the case of fluorine also up to the maximum number;
$R^5$ is a non-aromatic heterocycle which contains at least one oxygen, nitrogen and/or silicon ring atom, which is unsubstituted or substituted by one to six monovalent groups and which may be part of a spirocyclic, fused or bicyclic ring system.

17. An amide of the formula (I) or a salt thereof

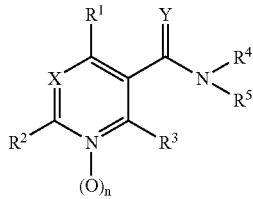

(I)

where the symbols and indices are defined below:
X is CH;
Y is O or S;
n is 0 or 1;
$R^1$ is $(C_1-C_4)$-haloalkyl;
$R^2$, $R^3$ are hydrogen
$R^4$ is $(C_1-C_{10})$-alkyl, $(C_3-C_{10})$-cycloalkyl, $(C_3-C_{10})$-alkenyl or $(C_3-C_{10})$-alkynyl, where the alkyl, cycloalkyl, alkenyl or alkynyl groups are unsubstituted or substituted by up to three halogen atoms, in the case of fluorine also up to the maximum number;
$R^5$ is a non-aromatic heterocycle which contains at least one oxygen, nitrogen and/or silicon ring atom, which is unsubstituted or substituted by one to six monovalent groups and which may be part of a spirocyclic, fused or bicyclic ring system.

18. An amide of the formula (I) or a salt thereof

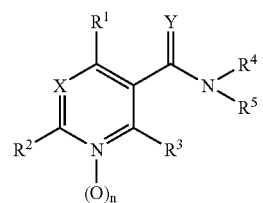

(I)

where the symbols and indices are as defined below:
X is CH;
Y is O or S;
n is 0 or 1;
$R^1$ is $(C_1-C_4)$-haloalkyl;
$R^2$, $R^3$ are hydrogen
$R^4$ is hydrogen, $(C_1-C_{10})$-alkyl, $(C_3-C_{10})$-cycloalkyl, $(C_3-C_{10})$-alkenyl or $(C_3-C_{10})$-alkynyl, where the alkyl, cycloalkyl, alkenyl or alkynyl groups are unsubstituted or substituted by up to three halogen atoms, in the case of fluorine also up to the maximum number;
$R^5$ is a non-aromatic heterocycle which contains at least one oxygen, nitrogen and/or silicon ring atom, which is unsubstituted or substituted by one to six monovalent groups and which may be part of a spirocyclic, fused or bicyclic ring system.

* * * * *